United States Patent
Moloney et al.

(10) Patent No.: US 11,850,080 B2
(45) Date of Patent: *Dec. 26, 2023

(54) PACKAGING SYSTEMS AND METHODS FOR MOUNTING A TOOL ON A SURGICAL DEVICE USING THE SAME

(71) Applicant: Stryker European Operations Limited, Carrigtwohill (IE)

(72) Inventors: Michael Moloney, Carrick-on-Suir (IE); Conor O'Donovan, Mallow (IE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,420

(22) Filed: Jan. 9, 2023

(65) Prior Publication Data

US 2023/0157780 A1     May 25, 2023

Related U.S. Application Data

(63) Continuation of application No. 17/839,525, filed on Jun. 14, 2022, now Pat. No. 11,602,405, which is a
(Continued)

(51) Int. Cl.
*A61B 50/30* (2016.01)
*A61B 34/37* (2016.01)
*A61B 50/00* (2016.01)

(52) U.S. Cl.
CPC .......... *A61B 50/3001* (2016.02); *A61B 34/37* (2016.02); *A61B 2050/0057* (2016.02); *A61B 2050/314* (2016.02)

(58) Field of Classification Search
CPC ................ A61B 50/3001; A61B 34/37; A61B 2050/0057; A61B 2050/314
(Continued)

(56) References Cited

U.S. PATENT DOCUMENTS 3,495,702 A    2/1970   Kuster
4,260,057 A    4/1981   Wall-Andersen
(Continued)

FOREIGN PATENT DOCUMENTS

DE           10146905 A1     7/2003
DE       102005022385 A1    11/2006
(Continued)

OTHER PUBLICATIONS

English language abstract and machine-assisted English translation for DE 10 2011 112 507 A1 extracted from espacenet.com database on Dec. 5, 2022, 13 pages.
English language abstract and machine-assisted English translation for DE 101 46 905 A1 extracted from espacenet.com database on Dec. 5, 2022, 8 pages.
English language abstract and machine-assisted English translation for WO 2018/164497 extracted from espacenet.com database on Apr. 16, 2020, 15 pages.
(Continued)

*Primary Examiner* — Jacob K Ackun
(74) *Attorney, Agent, or Firm* — Howard & Howard Attorneys PLLC

(57) ABSTRACT

Packaging systems and surgical kits for a tool that has a working portion and a shaft. A casing includes a distal section defining a cavity to receive the working portion of the tool. A proximal section is coupled to the distal section and receives the shaft of the tool. The proximal section is detachable from the distal section. In one implementation, at least a portion of the distal section comprises a colored indicator to provide a visual indication of a location of the working portion of the tool. In another implementation, instructions are provided on the proximal section and the instructions illustrate one or more steps for installing the tool to a surgical device.

20 Claims, 26 Drawing Sheets

Related U.S. Application Data continuation of application No. 16/890,339, filed on Jun. 2, 2020, now Pat. No. 11,395,711.

(60) Provisional application No. 62/857,419, filed on Jun. 5, 2019.

(58) Field of Classification Search
USPC .......................................................... 206/349
See application file for complete search history.

(56) References Cited

U.S. PATENT DOCUMENTS

| | | |
|---|---|---|
| 4,519,501 A | 5/1985 | Cerwin |
| 5,220,769 A | 6/1993 | Brown et al. |
| 5,246,109 A | 9/1993 | Markle et al. |
| 5,392,917 A | 2/1995 | Alpern et al. |
| 5,485,917 A | 1/1996 | Early |
| 5,542,427 A | 8/1996 | Aekerfeldt |
| 5,542,539 A | 8/1996 | Early |
| 5,584,164 A | 12/1996 | Sinn |
| 5,603,318 A | 2/1997 | Heilbrun et al. |
| 5,727,682 A | 3/1998 | Abidin et al. |
| 5,727,685 A | 3/1998 | Laganza et al. |
| 5,947,288 A | 9/1999 | Dykstra et al. |
| 6,059,111 A | 5/2000 | Davila et al. |
| 6,059,112 A | 5/2000 | Dykstra et al. |
| 6,161,695 A | 12/2000 | Nicolais |
| 6,412,639 B1 | 7/2002 | Hickey |
| 6,814,236 B2 | 11/2004 | Roshdy |
| 6,837,027 B2 | 1/2005 | Hickey |
| 6,915,901 B2 | 7/2005 | Feinberg et al. |
| 7,104,401 B2 | 9/2006 | Smith et al. |
| 7,128,208 B2 | 10/2006 | Hull |
| 7,316,318 B1 | 1/2008 | Rosten et al. |
| 7,320,404 B2 | 1/2008 | Landis |
| 7,331,463 B2 | 2/2008 | Hickey |
| 7,353,946 B2 | 4/2008 | Cervantes |
| 7,451,870 B2 | 11/2008 | Donahoe et al. |
| 7,467,710 B2 | 12/2008 | Cerwin et al. |
| 7,516,845 B2 | 4/2009 | Lang et al. |
| 7,611,008 B2 | 11/2009 | Ruffieux et al. |
| 7,617,932 B2 | 11/2009 | Windus-Smith et al. |
| 7,621,395 B2 | 11/2009 | Mogensen et al. |
| 7,648,030 B2 | 1/2010 | Landis |
| 7,726,564 B2 | 6/2010 | Goldbach |
| 7,770,722 B2 | 8/2010 | Donahoe et al. |
| 7,770,728 B2 | 8/2010 | Kærn |
| 7,975,842 B2 | 7/2011 | Thoes et al. |
| 8,006,839 B2 | 8/2011 | Hafner |
| 8,020,703 B2 | 9/2011 | List et al. |
| 8,042,689 B2 | 10/2011 | Frojd et al. |
| 8,079,487 B2 | 12/2011 | Roesler |
| D655,165 S | 3/2012 | Jensen et al. |
| 8,146,329 B2 | 4/2012 | Bryant et al. |
| 8,172,866 B2 | 5/2012 | List |
| 8,261,910 B2 | 9/2012 | Guenter et al. |
| 8,303,599 B2 | 11/2012 | Hess et al. |
| 8,320,612 B2 | 11/2012 | Knobel et al. |
| 8,365,910 B2 | 2/2013 | Valaie et al. |
| 8,517,174 B2 | 8/2013 | Dacey et al. |
| 8,770,405 B2 | 7/2014 | Dacey et al. |
| 8,783,459 B1 | 7/2014 | Marcinkowski |
| 8,881,900 B2 | 11/2014 | Witt et al. |
| 8,893,883 B2 | 11/2014 | Valaie et al. |
| 8,985,327 B2 | 3/2015 | Roesler |
| D731,326 S | 6/2015 | Johansson |
| 9,096,368 B2 | 8/2015 | Wu |
| 9,138,296 B2 | 9/2015 | Grabowski |
| 9,265,579 B2 | 2/2016 | Richart |
| 9,439,658 B2* | 9/2016 | Ford .................. A61B 17/1757 |
| 9,474,686 B2 | 10/2016 | Neal et al. |
| 9,532,847 B2 | 1/2017 | Hendrickson et al. |
| 9,585,727 B2 | 3/2017 | Richart |
| 9,592,098 B2 | 3/2017 | Richart |
| 9,597,092 B2 | 3/2017 | Pernot et al. |
| 9,707,039 B2 | 7/2017 | Grabowski et al. |
| 9,717,843 B2 | 8/2017 | Grucela et al. |
| 9,750,579 B2 | 9/2017 | Richart |
| 9,776,783 B2 | 10/2017 | Nadig et al. |
| 9,828,157 B2 | 11/2017 | Roesler |
| D806,541 S | 1/2018 | Love et al. |
| 9,872,754 B2 | 1/2018 | Tuechsen et al. |
| 9,926,116 B2 | 3/2018 | Kinyon |
| D818,813 S | 5/2018 | Love et al. |
| 9,975,679 B2 | 5/2018 | Hulliger |
| 9,999,469 B2 | 6/2018 | Roesler |
| 10,004,567 B2 | 6/2018 | Dacey et al. |
| 10,016,247 B2 | 7/2018 | Grabowski et al. |
| 10,017,303 B2 | 7/2018 | Wagner et al. |
| 10,029,043 B2 | 7/2018 | Grucela et al. |
| 10,059,499 B2 | 8/2018 | Roesler et al. |
| 10,086,131 B2 | 10/2018 | Okihara |
| 10,130,439 B2 | 11/2018 | Richart |
| 10,159,495 B1 | 12/2018 | Lambert |
| 10,159,555 B2 | 12/2018 | Bailly et al. |
| 10,335,245 B2* | 7/2019 | Jansen .................. A61B 50/30 |
| 10,479,579 B2* | 11/2019 | Pendergraph .......... B65D 79/02 |
| 11,058,419 B2* | 7/2021 | Vendely ................ A61B 42/00 |
| 11,395,711 B2* | 7/2022 | Moloney ................ A61B 34/37 |
| 11,602,405 B2* | 3/2023 | Moloney ................ A61B 34/37 |
| 2001/0019816 A1 | 9/2001 | Kumar |
| 2005/0218024 A1 | 10/2005 | Lang et al. |
| 2005/0220849 A1 | 10/2005 | Hickey |
| 2005/0251186 A1 | 11/2005 | Revie et al. |
| 2006/0200046 A1 | 9/2006 | Windus-Smith et al. |
| 2006/0243616 A1 | 11/2006 | Caron |
| 2007/0203393 A1 | 8/2007 | Stefanchik |
| 2012/0203230 A1 | 8/2012 | Adams |
| 2012/0305427 A1 | 12/2012 | Felder et al. |
| 2013/0299371 A1 | 11/2013 | Johansson |
| 2014/0102932 A1* | 4/2014 | Sherman .............. B65D 75/366 |
| | | 206/459.5 |
| 2014/0163555 A1 | 6/2014 | Pernot et al. |
| 2014/0251845 A1 | 9/2014 | Roesler |
| 2014/0251846 A1 | 9/2014 | Roesler |
| 2015/0196391 A1 | 7/2015 | Dwork |
| 2015/0297296 A1 | 10/2015 | Stauder et al. |
| 2016/0074118 A1 | 3/2016 | Tuechsen et al. |
| 2016/0135895 A1 | 5/2016 | Faasse et al. |
| 2016/0166350 A1 | 6/2016 | Burkhardt et al. |
| 2016/0244234 A1 | 8/2016 | Mayer et al. |
| 2017/0007388 A1 | 1/2017 | Neal et al. |
| 2017/0119487 A1 | 5/2017 | Binder et al. |
| 2017/0137194 A1 | 5/2017 | Lorence |
| 2017/0290634 A1 | 10/2017 | Dacey |
| 2017/0349347 A1 | 12/2017 | Bentz |
| 2017/0355505 A1 | 12/2017 | Nadig et al. |
| 2018/0162619 A1 | 6/2018 | Kocur et al. |
| 2018/0222655 A1 | 8/2018 | Grabowski et al. |
| 2018/0235348 A1 | 8/2018 | Booker |
| 2018/0296293 A1 | 10/2018 | Ueda |
| 2018/0296297 A1* | 10/2018 | Moloney .............. B65D 75/366 |
| 2018/0296749 A1 | 10/2018 | Grucela et al. |
| 2018/0311008 A1 | 11/2018 | Grabowski et al. |
| 2018/0344422 A1 | 12/2018 | Deck |
| 2019/0001050 A1 | 1/2019 | Okihara |
| 2019/0021807 A1* | 1/2019 | Barnell .................... B65D 1/34 |
| 2019/0315563 A1* | 10/2019 | Johansson .............. B25H 3/006 |
| 2020/0054199 A1 | 2/2020 | Kambe et al. |
| 2020/0383746 A1 | 12/2020 | Moloney et al. |
| 2022/0304761 A1 | 9/2022 | Moloney et al. |

FOREIGN PATENT DOCUMENTS

| | | |
|---|---|---|
| DE | 102011112507 A1 | 3/2013 |
| EP | 2298652 A1 | 3/2011 |
| EP | 2292528 B1 | 2/2013 |
| EP | 2662312 B1 | 10/2014 |
| GB | 2584534 A | 12/2020 |
| NO | 2018191396 A1 | 10/2018 |
| WO | 2011135246 A2 | 11/2011 |
| WO | 2017087732 A1 | 5/2017 |
| WO | 2017129757 A1 | 8/2017 |
| WO | 2017176569 A1 | 10/2017 |

(56) References Cited

FOREIGN PATENT DOCUMENTS

| | | | |
|---|---|---|---|
| WO | 2017185029 | A1 | 10/2017 |
| WO | 2017185052 | A1 | 10/2017 |
| WO | 2018011257 | A1 | 1/2018 |
| WO | 2018052832 | A1 | 3/2018 |
| WO | 2018106110 | A1 | 6/2018 |
| WO | 2018112107 | A1 | 6/2018 |
| WO | 2018156589 | A2 | 8/2018 |
| WO | 2018156611 | A1 | 8/2018 |
| WO | 2018164497 | A1 | 9/2018 |
| WO | 2018198308 | A1 | 11/2018 |
| WO | 2018202805 | A1 | 11/2018 |
| WO | 2018227066 | A1 | 12/2018 |
| WO | 2019035096 | A1 | 2/2019 |

OTHER PUBLICATIONS

English language abstract and machine-assisted English translation for WO 2018/202805 extracted from espacenet.com database on Apr. 16, 2020, 14 pages.

English language abstract for DE 10 2005 022 385 A1 extracted from espacenet.com database on May 26, 2021, 1 page.

English language abstract for EP 2 292 528 extracted from espacenet.com database on Feb. 27, 2020, 1 page.

English language abstract for WO 2011/135246 extracted from espacenet.com database on Jul. 8, 2020, 2 pages.

English language abstract for WO 2018/198308 extracted from espacenet.com database on Apr. 16, 2020, 2 pages.

International Search Report for Application No. PCT/US2018/027138 dated Jun. 25, 2018, 3 pages.

* cited by examiner

PACKAGING SYSTEMS AND METHODS FOR MOUNTING A TOOL ON A SURGICAL DEVICE USING THE SAME

CROSS-REFERENCE TO RELATED APPLICATIONS

This application is a continuation of U.S. patent application Ser. No. 17/839,525, filed Jun. 14, 2022, which is a continuation of U.S. patent application Ser. No. 16/890,339, filed on Jun. 2, 2020, now U.S. Pat. No. 11,395,711, which claims priority to and all the benefits of U.S. Provisional Patent App. No. 62/857,419, filed on Jun. 5, 2019, the entire contents of each of the aforementioned applications being hereby incorporated by reference.

BACKGROUND

A surgical device such as a robot often receives a tool or instrument for use during a surgical procedure. The tool may be a cutting accessory, such as a bur or drill, having a head with sharp features configured to resect tissue such as bone. Suboptimal packaging and handling of the tool may result in surgical site infection, injury, and other undesirable consequences.

Surgical site infections (SSIs) are one of the most commonly identified types of healthcare associated infections. The SSIs relevant to the present disclosure result from contamination of the tool with infectious material during handling and mounting of the tool on the surgical device. Known methods may include a user, such as an operating room technician, removing the tool from packaging and placing it on a table until it is necessary to mount the tool on the surgical device. The tool may be placed in intermediate packaging such as a poly bag, after which the user removes the tool from the poly bag for mounting on the surgical device. The known methods require the tool be physically handled by the user after removal from the packaging or intermediate packaging. For an elongate tool having a shaft coupled to the head, the shaft is mounted on the surgical device and requires the user to handle the tool proximate the head and its sharp features. It is well documented that hand hygiene is not always correctly performed, and proper hand hygiene may not always remove all pathogenic organisms. The inadvertent transference of pathogenic organisms from the user to the tool increases the risk of SSIs.

Known packaging also may not adequately prevent contact between the sharp features of the cutting accessory and the packaging during handling and removal of the tool. The user may, for example, pluck the shaft of the tool from the packaging. Should the head of the cutting accessory contact the packaging body during handling or removal, the sharp features may shave or otherwise remove small bits of the packaging. The bits may be imperceptible and remain on the head of the cutting accessory after being mounted on the surgical device. The bits may be introduced to the patient during the surgical procedure and increase the risk of SSIs from the body's response to the foreign material.

Often with surgical devices comprising a robot, the tool is mounted to the robot in advance of its use during the surgical procedure. In the interim, the head of the tool and its sharp features remain exposed in an unprotected manner for some time up to the point of use. The unprotected tool is associated with risk of contamination and/or injury, particularly as a surgical team moves about the operating room. For example, the operating room technician may inadvertently bump into the tool causing contamination of the tool, injury to the technician, and/or damage to the surgical device.

Furthermore, providing suitable packaging for surgical tools may require one or more components with intricate features that are costly to manufacture. The complexity and costs of the manufacturing and assembly processes may be further influenced by regulatory requirements and industry standards.

The issues above are complicated further by situations in which the tool that is mounted to the surgical device must be rotated by the technician in order to be properly installed in the surgical device. For example, the tool and surgical device may have corresponding alignment parts. When the technician applies force to install the tool, the corresponding alignment features cause the tool to rotate and align to the surgical device. If the tool is coupled to the packaging in a rotationally fixed (non-moveable) manner, then rotation of the tool during alignment will require rotation of the entire packaging. This creates ergonomic issues for the technician thereby making the installation process sub-optimal. Furthermore, in such situations, the technician may be inclined to remove the packaging, thereby destroying the purpose of the packaging by reintroducing potential contamination of the tool or injury to the technician.

Packaging systems and methods designed to overcome one or more of the aforementioned disadvantages are desired.

SUMMARY

This Summary introduces a selection of concepts in a simplified form that are further described below in the Detailed Description. This Summary is not intended to limit the scope of the claimed subject matter and does not necessarily identify each and every key or essential feature of the claimed subject matter.

According to a first aspect, a packaging system is provided for a tool that has a working portion and a shaft, the packaging system comprising: a casing comprising a distal section defining a cavity configured to receive the working portion of the tool; and a proximal section coupled to the distal section and configured to receive the shaft of the tool, and the proximal section being detachable from the distal section; wherein at least a portion of the distal section comprises a colored indicator to provide a visual indication of a location of the working portion of the tool.

According to a second aspect, a surgical kit is provided comprising: a tool including a working portion and a shaft; and a packaging system comprising: a casing comprising a distal section defining a cavity configured to receive the working portion of the tool; and a proximal section coupled to the distal section and configured to receive the shaft of the tool, and the proximal section being detachable from the distal section; wherein at least a portion of the distal section comprises a colored indicator to provide a visual indication of a location of the working portion of the tool.

According to a third aspect, a packaging system is provided for a tool that has a working portion and a shaft, the packaging system comprising: a casing comprising a distal section defining a cavity configured to receive the working portion of the tool; and a proximal section coupled to the distal section and configured to receive the shaft of the tool, and the proximal section being detachable from the distal section; wherein instructions are provided on the proximal section and the instructions are configured to illustrate one or more steps for installing the tool to a surgical device.

According to a fourth aspect, a surgical kit is provided comprising: a tool including a working portion and a shaft; and a packaging system comprising: a casing comprising a distal section defining a cavity configured to receive the working portion of the tool; and a proximal section coupled to the distal section and configured to receive the shaft of the tool, and the proximal section being detachable from the distal section; wherein instructions are provided on the proximal section and the instructions are configured to illustrate one or more steps for installing the tool to a surgical device.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

I. Packaging System

Figure 1:
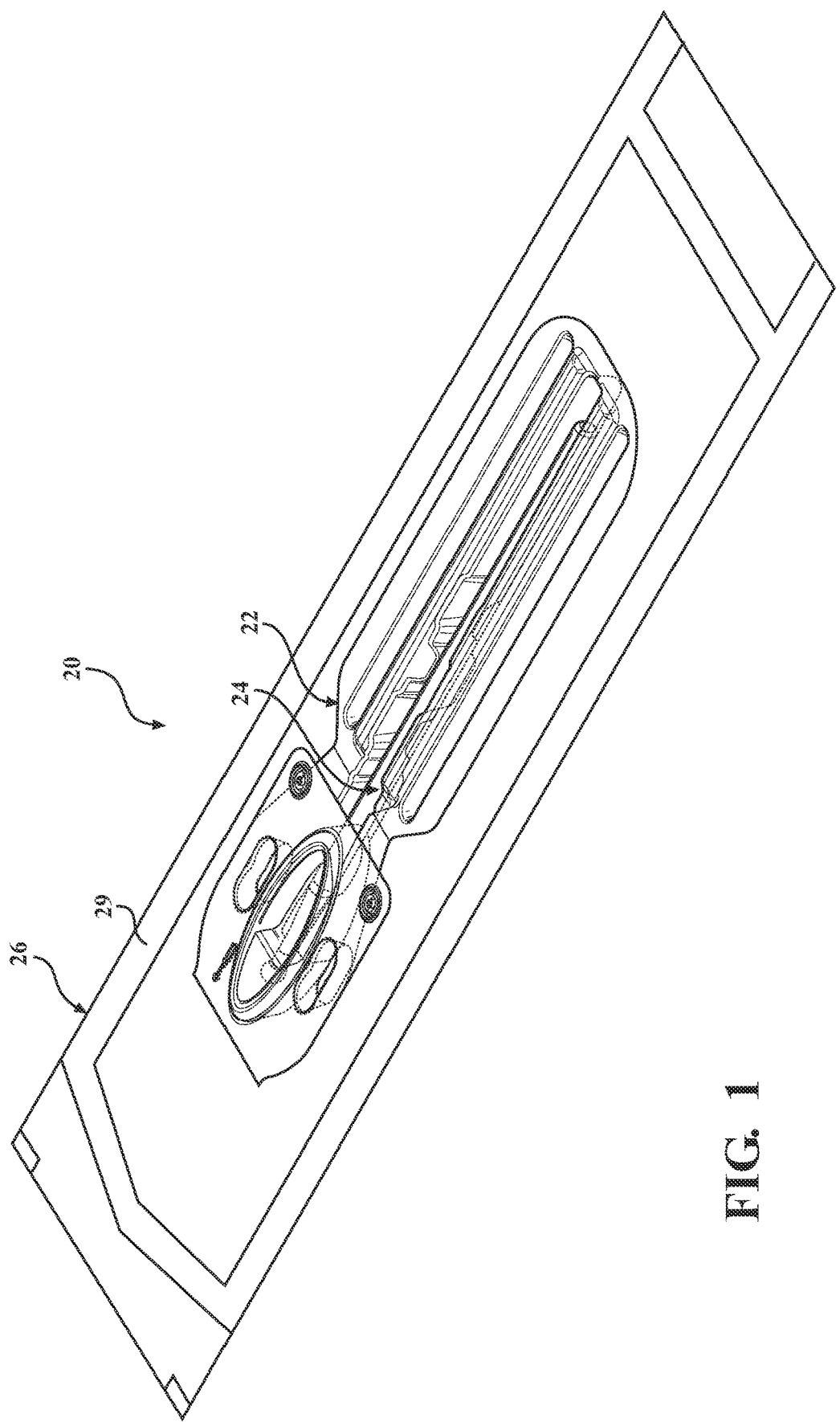
FIG. 1 is a perspective view of a packaging system in accordance with an example embodiment of the present disclosure.

FIG. 1 shows a packaging system 20 according to one example embodiment. The packaging system 20 includes a segmented packaging body 22 configured to removably receive an elongate tool 24. Secondary packaging 26 may be provided and configured to receive the packaging body 22. In the embodiment illustrated in FIG. 1, the secondary packaging 26 includes a sealed pouch having opposing layers coupled through, for example, heat sealing, adhesive, and the like. The seal 29 may extend around the packaging body 22 once disposed between the layers to provide a hermetic seal. The layers of the secondary packaging 26 may be peeled apart to expose the packaging body 22 for functions to be disclosed.

The secondary packaging 26 may include a blister pack. A tray with a cavity is formed within a suitable material, preferably thermoformed plastic. The cavity may be formed in a suitable geometry to accommodate the packaging body 22. A film is removably attached about a periphery of the formed tray to provide a peel-open feature. The film may be porous to allow sterilization. One suitable film is Tyvek® manufactured by DuPont™ (Wilmington, Del.). In another example, the film may be applied directly to the packaging body 22. In such an example, the film provides supplemental security for the tool 24 within the packaging body 22. Other types of secondary packaging are contemplated, but it is to be understood the packaging systems described herein may include the packaging body without secondary packaging.

Figure 11:
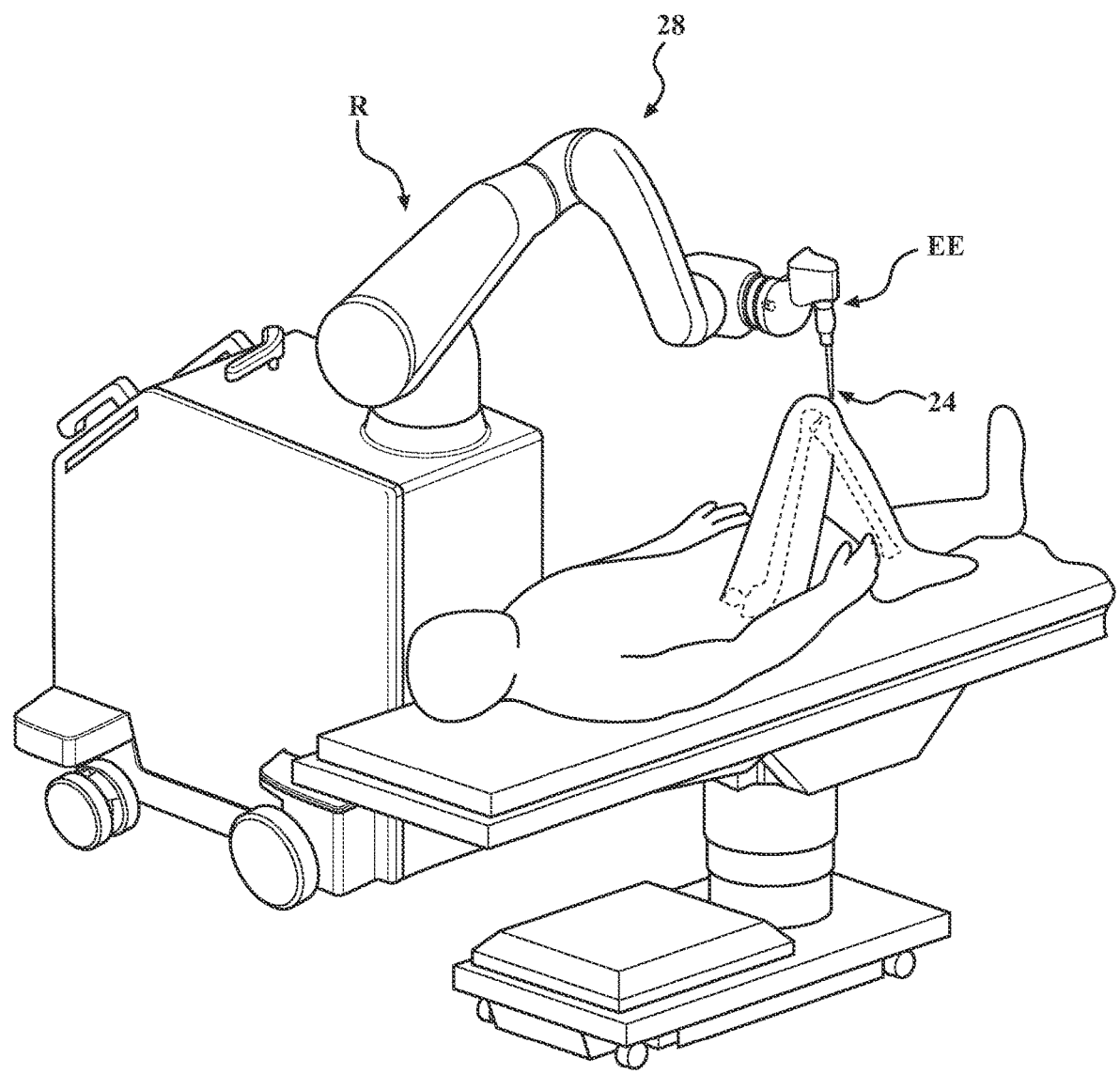
FIG. 11 is a surgical device.

The packaging system 20 provides safe, sterile and secure handling of the tool 24 during storage, transport, and mounting of the tool 24 on a surgical device 28 (see FIG. 11). FIG.

Figure 2:
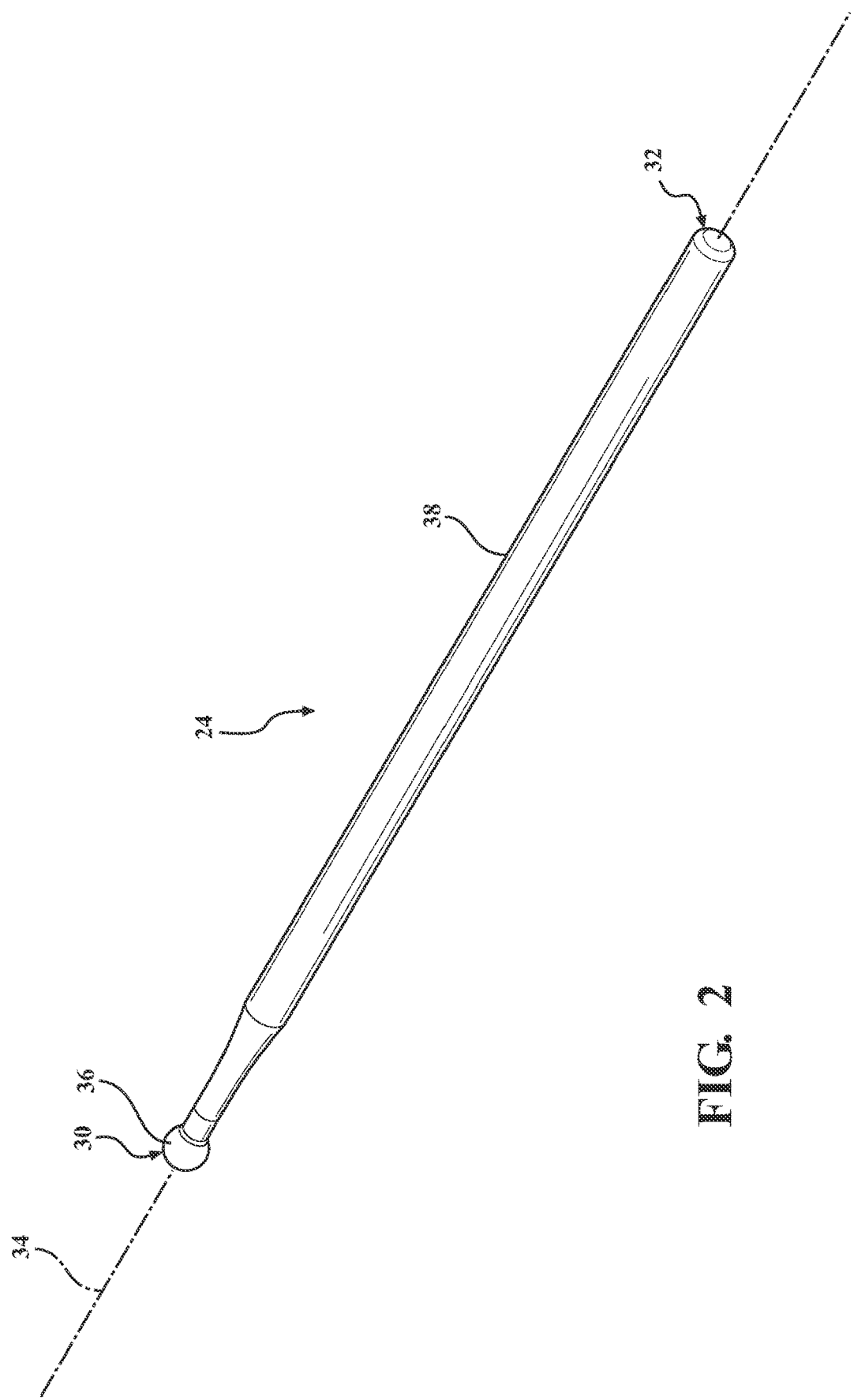
FIG. 2 is a perspective view of an elongate tool.

2 shows an example tool for use with the packaging systems described herein. The tool 24 includes a distal end 30 and a proximal end 32 opposite the distal end 30. A length of the tool 24 is defined between the distal end 30 and the proximal end 32. A tool axis 34 may be defined between the distal end 30 and the proximal end 32. A width of the tool 24 is less than the length such that the tool 24 may be defined as elongate. The tool 24 of FIG. 2 is circular in cross section, but it is to be understood that other suitable shapes are contemplated, including triangles, squares, and higher order polygons. The tool could be curved or a non-linear elongated device, or it could be a movable multi-piece assembly. Other types of surgical tools are contemplated.

The proximal end 32 is configured to be coupled to the surgical device 28. The surgical device 28 may be any apparatus configured to receive the tool 24. The tool 24 may be the instrument that directly interfaces with the patient, whereas the surgical device 28 may provide actuation, control, power, and the like to the tool 24. The surgical device 28 of FIG. 11 is a surgical robot R having an end effector EE configured to receive the tool 24. In certain embodiments, the tool 24 is a resection instrument such as a surgical bur or drill. FIG. 2 shows the surgical bur with the distal end 30 comprising a head 36 with the head 36 rigidly coupled to a shaft 38 extending to the distal end 32. Example surgical burs include the CORE™ Burs manufactured by Stryker® Corporation (Kalamazoo, Mich.).

Other examples of the tool 24 and the surgical device 28 configured to receive the tool 24 are contemplated. For example, possible combinations of the tool 24 and the surgical device 28 may include: a router, a curved bur, or a sleeve connector for a bur configured to be received by a handheld rotary instrument; electrodes configured to be received by a smoke evacuation pencil; a saw or a blade configured to be received by a saw driver; a scalpel configured to be received by a scalpel handle; an ultrasonic tip configured to be received by a sonopet; and an endoscopic shaver or cutter configured to be received by an endohandpiece. It is to be understood that other surgical devices for receiving tools are contemplated.

A cutting accessory sleeve (not shown) or collet may be provided and disposed about the shaft 38. The packaging body 22 may be suitably shaped to accommodate the tool 24 with or without the cutting accessory sleeve coupled to the shaft 38. Receiving the cutting accessory sleeve within the packaging body 22 may facilitate improved mounting of the tool 24 on the surgical device 28 in manners to be described.

Figure 3:
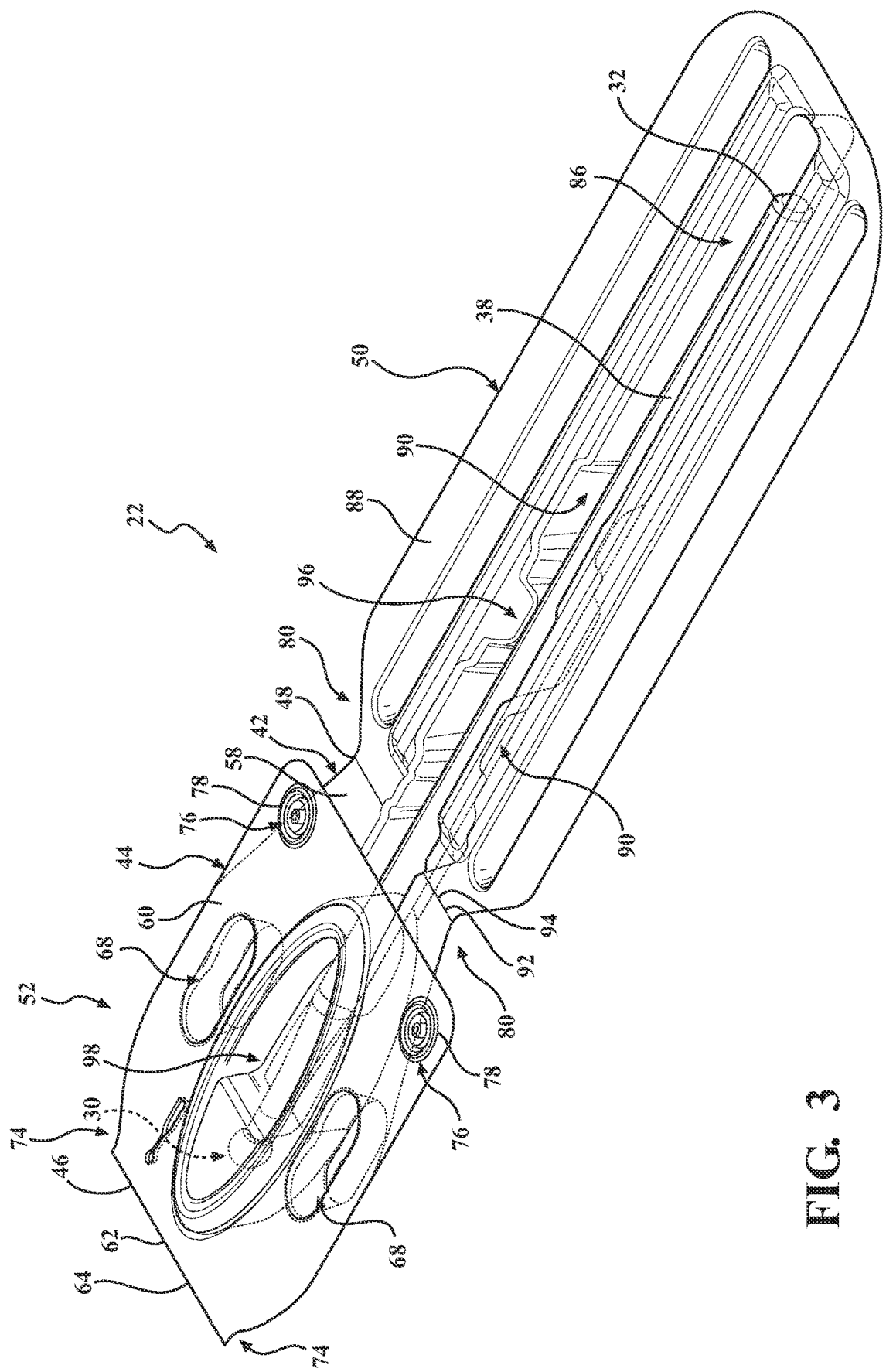
FIG. 3 is a perspective view of a packaging body in accordance with an example embodiment of the present disclosure with an elongate tool disposed within the packaging body in a first configuration.
Figure 4:
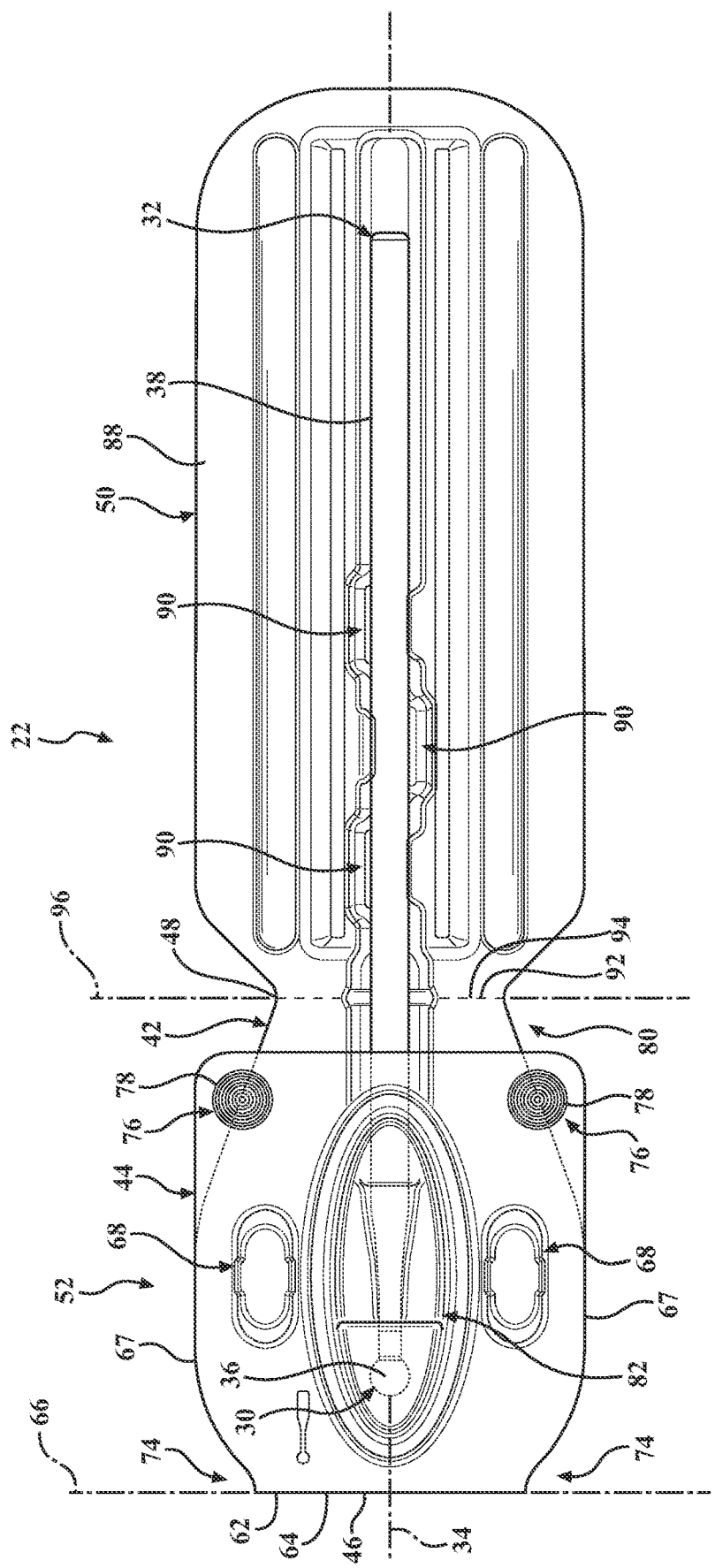
FIG. 4 is a top plan view of the packaging body of FIG. 3.
Figure 5:
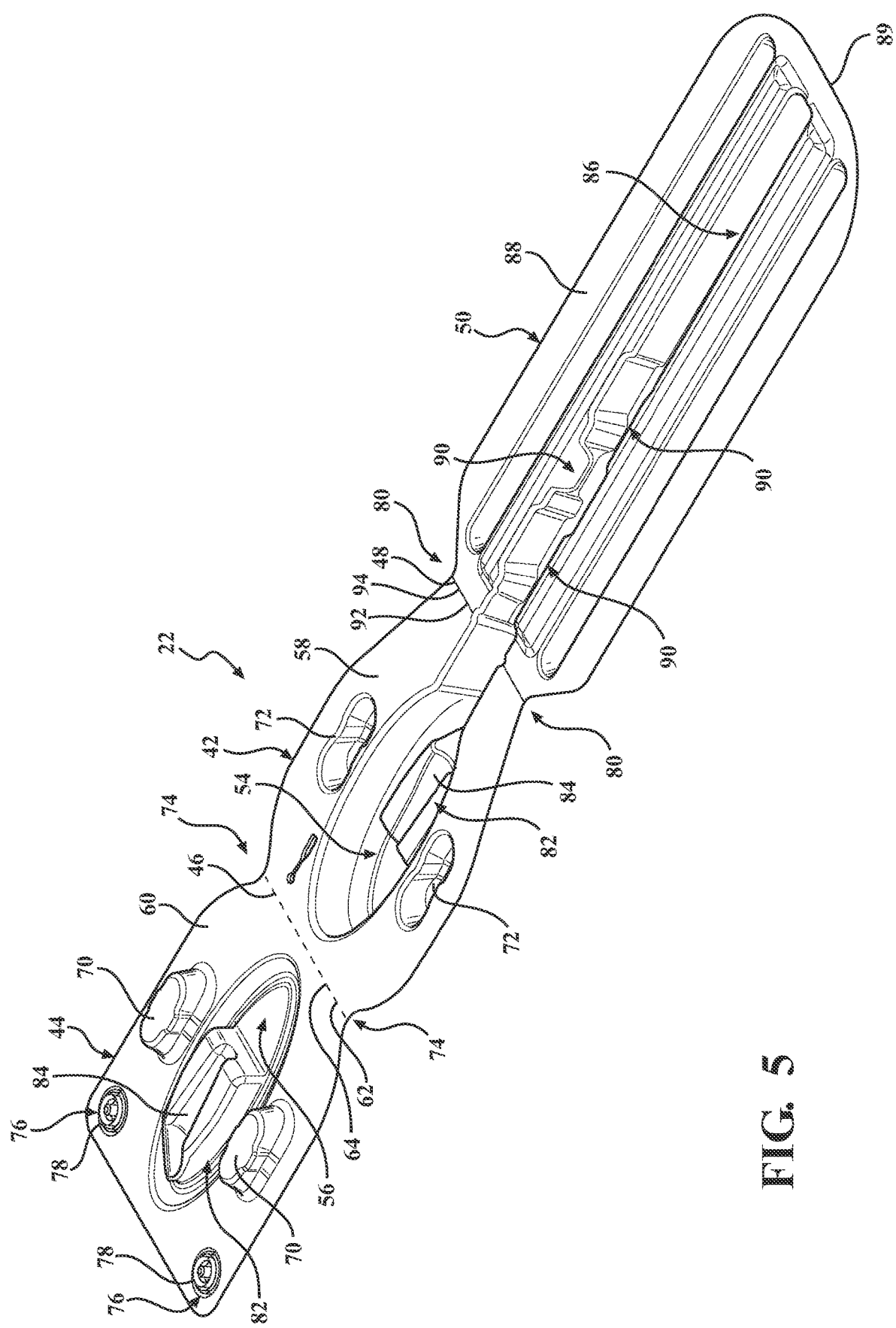
FIG. 5 is a perspective view of the packaging body of FIG. 3 in a second configuration with the elongate tool removed from the packaging body.

Referring to FIGS. 3-5, the segmented packaging body 22 of the present embodiment of the packaging system 20 is shown. The packaging body 22 includes a first distal section 42 and a second distal section 44. The first distal section 42 includes a first boundary and a second boundary. In some embodiments, the boundaries include a distal boundary 46 and a proximal boundary 48. The second distal section 44 is coupled to the first distal section 42 at the distal boundary 46. The packaging body 22 further includes a proximal section 50 coupled to the first distal section 42 at the proximal boundary 48. The packaging body may be included in part or entirely of polyethylene terephthalate glycol-modified (PETG). Other suitable materials may include, without limitation, polymers such as polyethylene terephthalate (PET), high-density polyethylene (HDPE), polyvinyl chloride (PVC), low-density polyethylene (LDPE), polypropylene (PP), and polystyrene (PS), epoxy and other resins, and malleable metals such as aluminum. The packaging body 22 is preferably formed by thermoforming, but injection molding, vacuum molding, blow molding, and other manufacturing processes are also contemplated.

The first and second distal sections 42, 44 are configured to receive the distal end 30 of the tool 24. FIGS. 3 and 4 show the first and second distal sections 42, 44 receiving the distal end 30 and a portion of the shaft 38 of the tool 24. The first and second distal sections 42, 44 may be pivotally coupled to provide a casing 52 to the distal end 30 of the tool 24.

The casing 52 may be provided by a cavity 54, 56 disposed in each of the first and second distal sections 42, 44. With reference to FIGS. 3 and 5, the first distal section 42 includes a primary surface 58 extending between the distal boundary 46 and the proximal boundary 48. The cavity 54 may be disposed within the primary surface 58 and positioned intermediate the distal boundary 46 and the proximal boundary 48. The second distal section 44 includes a primary surface 60 with the cavity 56 disposed within the primary surface 60. The primary surfaces 58, 60 may be considered as substantially flat portions of first and second distal sections 42, 44 to which many of the features described herein are formed or otherwise coupled. The cavities 54, 56 of each of the first and second distal sections 42, 44 may be in substantial alignment so as to receive the distal end 30 of the tool 24 in a first configuration to be described. In other embodiments, only one of first and second distal sections 42, 44 may include a cavity suitably dimensioned to receive the distal end 30 of the tool 24 with the other one of first and second distal sections 42, 44 being substantially flat. In certain embodiments, the proximal section 50 may include a flat surface devoid of the cavity 86. In such an example, the flat surface may extend adjacent to the shaft 38 of the tool 24.

The casing 52 may be provided by articulating one of the first and second distal sections 42, 44 relative to the other to the first configuration shown in FIGS. 3 and 4. The second distal section 44 may be pivotally coupled to the first distal section 42 at the distal boundary 46. In certain embodiments, the second distal section 44 is pivotally coupled to the first distal section 42 about an axis 66 perpendicular to the tool axis 34 of the tool 24. In certain embodiments, the tool 24 may be curved, such as a curved portion extending distally from a straight portion. In such an embodiment, the casing 52 may be generally arcuate in shape. Alternatively, the packaging may be oriented similar to that shown in FIG. 4, but otherwise configured to accommodate the curved tool.

In one example, the packaging body 22 includes a living hinge 62 at the distal boundary 46. The living hinge 62 may be described as a thin, flexible connection or web coupling first and second distal sections 42, 44. The living hinge 62 may be a consequence, at least in part, of perforations 64 at the distal boundary 46. In some cases, the first distal section 42 may be configured to be detachable from the second distal section 44 at the perforations 64. Other suitable ways of effectuating relative movement between the first and second distal sections 42, 44 are contemplated. For example, a flexible material may couple the first and second distal sections 42, 44 and/or may couple the first distal section 42 and the proximal section 50. In such an embodiment, the first and second distal sections 42, 44 and the proximal section 50 are discrete structures coupled by the material adapted to bend so as to enable the relative pivoting at the distal boundary 46 and/or the proximal boundary 48. In one example, the flexible material includes an adhesive adapted to join an adjacent two of the sections 42, 44, 50. A portion of the flexible material is adhered to each of the adjacent two of the sections 42, 44, 50 with or without a small gap disposed between the adjacent two of the sections 42, 44, 50. If desired, the adjacent two of the sections 42, 44, 50 may be separated by providing sufficient force to overcome the adhesive force.

The second distal section 44, for example, may be pivoted relative to the first distal section 42 to provide the casing 52. In other words, at least one of the first and second distal sections 42, 44 is configured to move between the first configuration and a second configuration. In the second configuration to be described in greater detail, the first and second distal sections 42, 44 are positioned in a non-abutting relationship. In the first configuration, the first and second distal sections 42, 44 are positioned in an abutting relationship such that the distal end 30 of the tool 24 is encased between the first and second distal sections 42, 44. In the example embodiment shown in FIGS. 4 and 5, the second distal section 44 may be moved or folded over onto the first distal section 42 such that the primary surfaces 58, 60 are in a direct abutting relationship. The movement is guided by the living hinge 62 oriented on the axis 66 such that the first and second distal sections 42, 44 are generally aligned atop one another in the first configuration. The direct abutting relationship of the primary surfaces 58, 60 provides the casing 52 to the distal end 30 of the tool 24. In the first configuration, the primary surfaces of the first and second distal sections 42, 44 are substantially parallel.

In certain embodiments, including those illustrated throughout the present disclosure, the distal boundary 46 is opposite the proximal boundary 48 such that in the second configuration, the first and second distal sections 42, 44 and the proximal section 50 are generally aligned or positioned in-line, as illustrated in FIG. 5. In other words, in the second configuration with the primary surfaces 58, 60 of the first and second distal sections 42, 44 positioned in a non-abutting relationship, the first distal section 42 is positioned adjacent the second distal section 44 opposite the proximal section 50. Certain modifications of the packaging body 22 are contemplated. For example, one of the lateral edges 67 (see FIG. 4) may include the living hinge 62 about which one of the first and second distal sections 42, 44 is configured to move between the first configuration and the second configuration. In such an example, the first and second distal sections 42, 44 are pivotally coupled at a side boundary and not at the distal boundary 46. The function of the casing 52 is substantially as described with the relative pivoting about one of the lateral edges 67 resulting in the sections 42, 44, 50 assuming an L-shaped configuration.

The packaging body 22 further includes couplers 68 removably coupling the first and second distal sections 42, 44. The couplers 68 are configured to maintain the first and second distal sections 42, 44 in the first configuration absent an input from a user to be described. The couplers 68 may operate by interference or friction fit, but other modes of securing the first and second distal sections 42, 44 are contemplated, such as adhesive. In certain embodiments, the couplers 68 include a protrusion 70 removably coupled to a recess 72 by interference fit in the first configuration. More specifically, the recess 72 may be provided within one of the first and second distal sections 42, 44, and the protrusion 70 provided on the other one of the first and second distal sections 42, 44. In the example embodiment shown in FIGS. 3-5, two recesses 72 are provided within the first distal section 42, and two protrusions 70 provided on the second distal section 44. The protrusions 70 and recesses 72 are positioned on opposing sides of the cavities 54, 56 of the first and second distal sections 42, 44, respectively. The protrusion 70 and the recess 72 may extend from the primary surfaces 58, 60 of the first and second distal sections 42, 44. The interference fit between the protrusion 70 and the recess 72 maintains the casing 52 such that the first and second distal sections 42, 44 encase the distal end 30 of the tool 24. Additionally or alternatively, additional structures may be formed within the cavities 54, 56 to create an interference fit between the first and second distal sections 42, 44 to maintain the casing 52 in the first configuration. In other example embodiments, one of the first and second distal sections 42, 44 may include edges with a "folded" or "crimped" shape so as to create the interference fit (or snap-fit) with edges of the other one of the first and second distal sections 42, 44. For example, the lateral edges 67 of the second distal section 44 may be formed such that the lateral edges 67 deflect when moving the casing 52 of the packaging body 22 between the first and second configurations. The casing 52 provides, among other advantages to be described, secure handling of the distal end 30 of the tool 24.

The second configuration provides positioning the first and second distal sections 42, 44 in the non-abutting relationship, thereby exposing a portion of the distal end 30 of the tool 24 disposed within the first distal section 42. FIG. 5 shows the second configuration (with the tool 24 removed). Positioning the packaging body 22 in the second configuration typically occurs after the tool 24 is mounted on the surgical device 28 in a manner to be described. Moving the packaging body 22 from the first configuration to the second configuration includes pivoting one of the first and second distal sections 42, 44 relative to the other. In one example, one of the first and second distal sections 42, 44 is pivoted about the distal boundary 46 comprising the living hinge 62 oriented on the axis 66 transverse to the tool axis 34. The desired movement may be further facilitated by cutouts 74 disposed at opposing ends of the distal boundary 46. The cutouts 74 include material removed or absent from one or more of the first and second distal sections 42, 44 at the opposing ends of the distal boundary 46, as shown in FIGS. 3-5. The cutouts 74 may include material removed or absent from one or more of the first distal section 42 and the second distal section 44 at a singular one of the opposing ends of the distal boundary 46. The cutouts 74 of the illustrative embodiment are generally triangular when viewed in plan, but other suitable shapes are contemplated. The cutouts 74 may localize stresses at the opposing ends of the distal boundary 46 to facilitate relative pivoting of first and second distal sections 42, 44 at the distal boundary 46.

The relative pivoting is typically imparted by the user holding the packaging body 22. In one example, the user may hold the proximal section 50 and/or the first distal section 42 in one hand and grasp the second distal section 44 with the other hand in order to overcome the interference fit of the couplers 68. The user may use fingers to pinch or grasp the second distal section 44 while holding the first distal section 42. The packaging body 22 may further include a finger grip 76 configured to be grasped by the fingers of the user. The second distal section 44 includes the finger grip 76 positioned and/or extending outwardly from the first distal section 42. FIGS. 3-5 show two finger grips 76 positioned on opposite sides of the cavity 56. In certain embodiments, the finger grip 76 may include a portion of the primary surface 60 of the second distal section 44 extending outwardly from the first distal section 42. The portion of the primary surface 60 may be positioned adjacent and/or proximate to cutouts 80 associated with the proximal boundary 48 for functions to be described. The finger grip 76 in combination with the cutouts 80 provides a suitable surface to facilitate disengagement of the interference fit of the couplers 68. In certain embodiments, the finger grip 76 is the portion of the primary surface 60 of the second distal section 44 to be grasped by the user to apply a force to disengage the protrusion 70 from the recess 72, thereby initiating the relative pivoting of the first and second distal sections 42, 44. Additionally or alternatively, the finger grip 76 may include a texturized feature 78 configured to be grasped between the fingers of the user. The texturized feature 78 further provides a gap between the first and second distal sections 42, 44 with the gap adapted to be engaged by one of the fingers of the user. In certain embodiments, material of durable strength, such as a string, may be provided and rigidly coupled to one of the first and second distal sections 42, 44. The material is adapted to be grasped by the user to facilitate moving the casing 52 from the first configuration to the second configuration. In another example embodiment, a portion of the second distal section 44 may include a tab of elevated material to be pinched between the fingers of the user to facilitate moving the casing 52 from the first configuration to the second configuration.

The casing 52 may include features configured to prevent contact of the head 36 of the tool 24 with the first and second distal sections 42, 44 when the tool 24 is secured within the packaging body 22. Each of the first and second distal sections 42, 44 may include a boss 82 configured to support the tool 24 proximate the distal end 30. Referring to FIG. 5, the boss 82 is disposed within the cavities 54, 56 of each of the first and second distal sections 42, 44. The boss 82 may extend from a base surface partially defining the cavity. The boss 82 may include a slot 84 flanked by ridges with the slot 84 configured to receive the shaft 38 of the tool 24 proximal the head 36. The ridges are suitably sized such that when the couplers 68 are coupled in the first configuration, the shaft 38 of the tool 24 proximal the head 36 is securely encircled within the slots 84. The casing 52 may be considered substantially contoured to the distal end 30 of the tool 24. The head 36 of the tool 24 is distal the boss 82, as shown in FIG. 4, and suspended with the casing 52. In other words, the head 36 of the tool 24 is spaced at a distance from surfaces of the packaging body 22 to prevent contamination of the tool 24. In one example, eight millimeters of clearance is provided about the head 36 of the tool 24. In other examples, four, six or ten or more millimeters of clearance may be provided. During mounting or installation of the tool 24 with the surgical device 28 as to be described, the user may grasp the casing 52 without risk of touching the tool 24 and without contamination of the tool 24 from the packaging body 22.

The packaging body 22 includes the proximal section 50 coupled to the first distal section 42 at the proximal boundary 48. The proximal section 50 may further include a primary surface 88 coupled to the primary surface 58 of the first distal section 42 at the proximal boundary 88. The primary surface 88 may be considered as substantially flat portions of proximal section 50 to which many of the features described herein may be formed or otherwise coupled. The proximal section 50 is configured to receive the proximal end 32 of the tool 24. Referring to FIGS. 3 and 4, the proximal section 50 receives a proximal portion of the shaft 38 of the tool 24 comprising the proximal end 32. The proximal section 50 includes a cavity 86 configured to receive the proximal portion of the tool 24. In certain embodiments, the cavity 86 is disposed within the primary surface 88 and positioned intermediate the proximal boundary 48 and a proximal edge 89 of the packaging body 22. FIGS. 3-5 show the cavity 86 is an elongate cavity and suitably sized to receive the tool 24.

The tool 24 may be secured within the cavity 86 with one or more shaft couplers 90. The shaft couplers 90 may include a protrusion with a counterposing recess. The protrusion may extend into the cavity 86 with the counterposing recess extending outwardly from the cavity 86 opposite the protrusion. The arrangement of the shaft coupler 90 provides an interference fit to the shaft 38 of the tool 24. Based on the material composition and thickness of the packaging body 22, a small amount of elastic deformation of the shaft coupler 90 occurs as the tool 24 is urged within the cavity 86 of the proximal section 50. Once received within the cavity 86 the protrusion of the shaft coupler 90 positioned superior the tool 24 returns to a natural state and provides the interference fit for the shaft 38 of the tool 24. FIGS. 3-5 show three shaft couplers 90 spaced axially along the cavity 86 of the proximal section 50, but one, two, four or more shaft couplers are contemplated. Each of the three shaft couplers 90 is arranged in an opposite manner from an adjacent shaft coupler 90. In other words, the protrusion and the counterposing recess of one shaft coupler 90 are "flipped" relative to the adjacent shaft coupler 90. The resulting arrangement provides the interference fit on radially opposite positions on the shaft 38 for improved retention of the tool 24 within the proximal section 50.

The cavities 54, 56, 86 of the first and second distal sections 42, 44 and the proximal section 50 are configured to receive a portion of the tool 24. The cavity 54 of the first distal section 42 and the cavity 86 of the proximal section 50 may be substantially collinear. In embodiments where the shaft 38 of the tool 24 is cylindrical and rigid, the cavities 54, 86 receiving a portion of the shaft 38 are substantially collinear or aligned to receiving the tool 24 within the packaging body 22. FIGS. 3-5 show the cavity 54 of the first distal section 42 and the cavity 86 of the proximal section 50 being continuous such that each of the cavities 54, 86 extend to the proximal boundary 48 and form a singular channel between the first distal section 42 and the proximal section 50.

The proximal section 50 may be pivotally coupled to the first distal section 42 at the proximal boundary 48. FIGS. 3-5 show the primary surface 58 of the first distal section 42 pivotally coupled to the primary surface 88 of the proximal section 50 at the proximal boundary 48. The packaging body 22 may further comprising a living hinge 92 at the proximal boundary 48 configured to facilitate pivoting the proximal section 50 relative to the first distal section 42. The living hinge 92 may be described as a thin, flexible connection or web coupling first distal section 42 and the proximal section 50, and more particularly the primary surfaces 58, 88. The living hinge 92 may be a consequence, at least in part, of a perforation 94 at the proximal boundary 48 for functions to be described.

Figure 6:
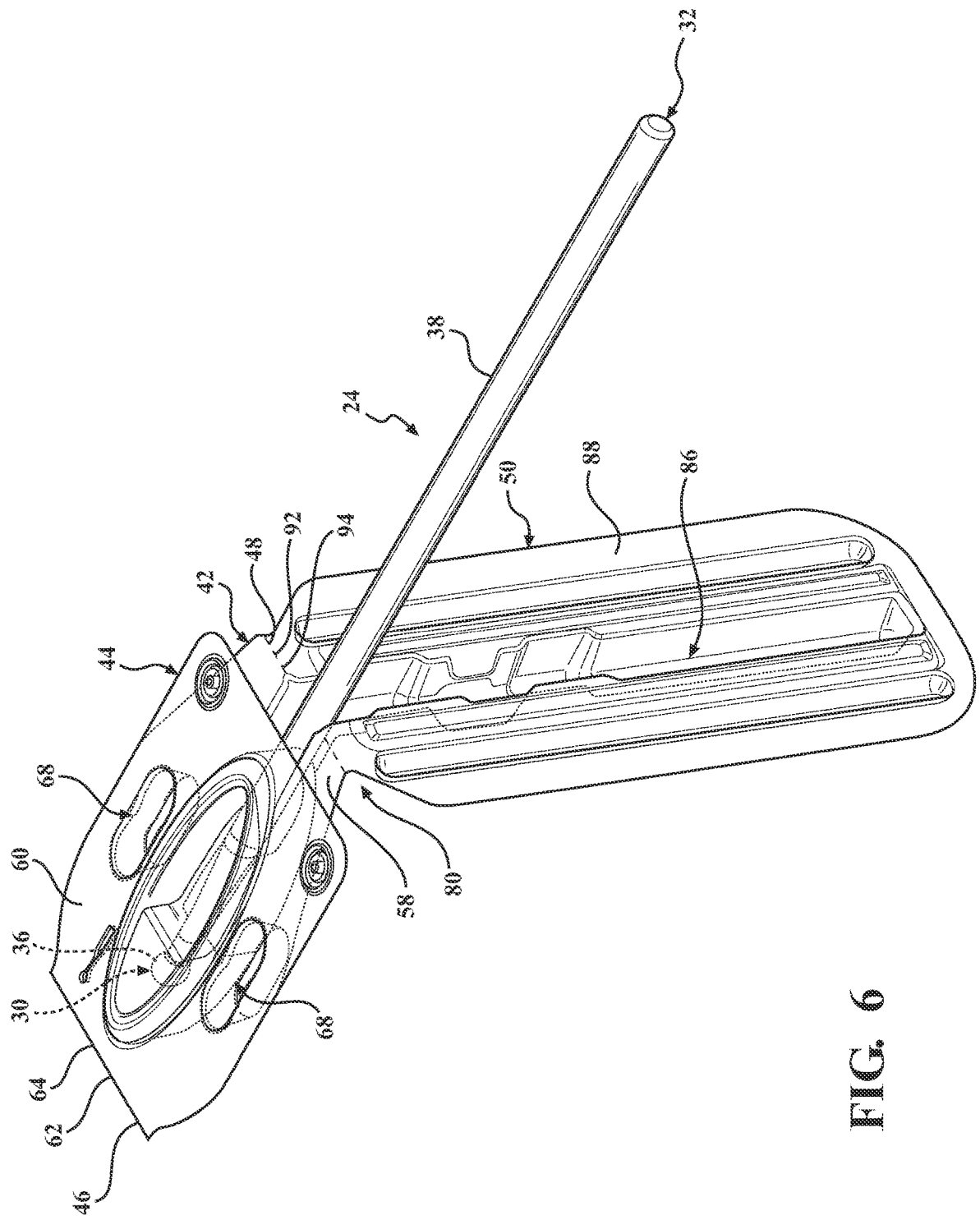
FIG. 6 is a perspective view of the packaging body of FIG. 3 with the elongate tool disposed within the packaging body in an installation configuration.

The proximal section 50 is configured to move between a packaging configuration and an installation configuration. The packaging configuration, as shown in FIGS. 3 and 4, includes the proximal end 32 of the tool 24 disposed within the cavity 86 of the proximal section 50. In the packaging configuration, the primary surfaces 58, 88 of the first distal section 42 and the proximal section 50 may be substantially coplanar. The packaging body 24 may be provided in the packaging configuration prior to installing or mounting the tool 24 on the surgical device 28 in a manner to be described. Referring to FIG. 6, the installation configuration includes pivoting the proximal section 50 relative to the first distal section 42, thereby exposing the proximal end 32 of the tool 24 outside the cavity 86 of the proximal section 50. Moving from the packaging configuration to the installation configuration may include pivoting the primary surface 88 of the proximal section 50 relative to the primary surface 58 of the first distal section 42 to expose the proximal end 32 of the tool 24 outside the cavity 86.

The living hinge 92 and the cutouts 80 facilitate the relative pivoting between the first distal section 42 and the proximal section 50 at the proximal boundary 48. The living hinge 92 may be oriented on an axis 96 perpendicular to the tool axis 34 of the tool 24, as shown in FIG. 4, such that the proximal section 50 is pivotally coupled to the first distal section 42 about the axis 96 perpendicular to the tool axis 34 of the tool 24. The axis 96 of the living hinge 92 at the proximal boundary 48 may be oriented parallel to the axis 66 of the living hinge 92 at the distal boundary 46. In other embodiments when the tool 24 is curved, the axis 96 may or may not be perpendicular to the tool axis 34 of the tool 24. For example, the axis 96 may be oriented at any suitable angle relative to the tool axis 34 to accommodate one or more curved portions of the tool 24.

The packaging body 22 of the illustrated embodiments of the present disclosure, with the tool 24 disposed within the cavities 54, 56 extending along a midline of the width, results in a generally symmetric construction of the packaging body 22. It is to be understood that the packaging body 22 need not be symmetric in construction. For example, the illustrated embodiments show the living hinges 62, 92, and the perforations 64, 94 extending across an entirety of a width of the packaging body 22 (e.g., between the cutouts 74, 80). In certain embodiments, the living hinges 62, 92, and/or the perforations 64, 94 may extend across the packaging body 22 for only a portion of the width. In one example, the living hinges 62, 92, and/or the perforations 64, 94 may be positioned entirely to one side of the tool axis 34 of the tool 24. In other words, the living hinges 62, 92, and/or the perforations 64, 94 extend from the cutouts 74, 80 to less than halfway across the width of the packaging body 22 (i.e., the midline of the otherwise symmetric packaging body). Additionally or alternatively, one or more tabs (not shown) may be provided and coupled to or integral with one of the first and second distal sections 42, 44, and/or the proximal section 50. The tab is positioned adjacent the perforation(s) 64, 94 and extend outwardly from the packaging body 22. The tab is adapted to be grasped by a user to effectuate a tearing motion at the perforation(s) 64, 94 with the user supporting the packaging body 22 opposite the perforation 64, 94 to be engaged. The tab may be positioned on one or both sides of the packaging body 22. Furthermore, there may be only one perforation 64, 94 provided to localize the tearing force provided by the user.

The cutouts 80 may be disposed at opposing ends of the proximal boundary 48. The cutouts 80 include material removed or absent from one or more of the first distal section 42 and the proximal section 50 at the opposing ends of the proximal boundary 48, as shown in FIGS. 3-5. The cutouts 80 may include material removed or absent from one or more of the first distal section 42 and the proximal section 50 at a singular one of the opposing ends of the proximal boundary 48. The cutouts 80 of the illustrative embodiment are generally triangular when viewed in plan, but other suitable shapes are contemplated. The cutouts 80 may localize stresses at the opposing ends of the proximal boundary 48 to facilitate relative pivoting of first distal section 42 and the proximal section 50 at the proximal boundary 48. The relative pivoting is typically imparted by the user holding the packaging body 22. In one example, the user may hold the casing 52 in one hand and grasp the proximal section 50 with the other hand in order to pivot the proximal section 50 relative to the casing 52.

Figure 7:
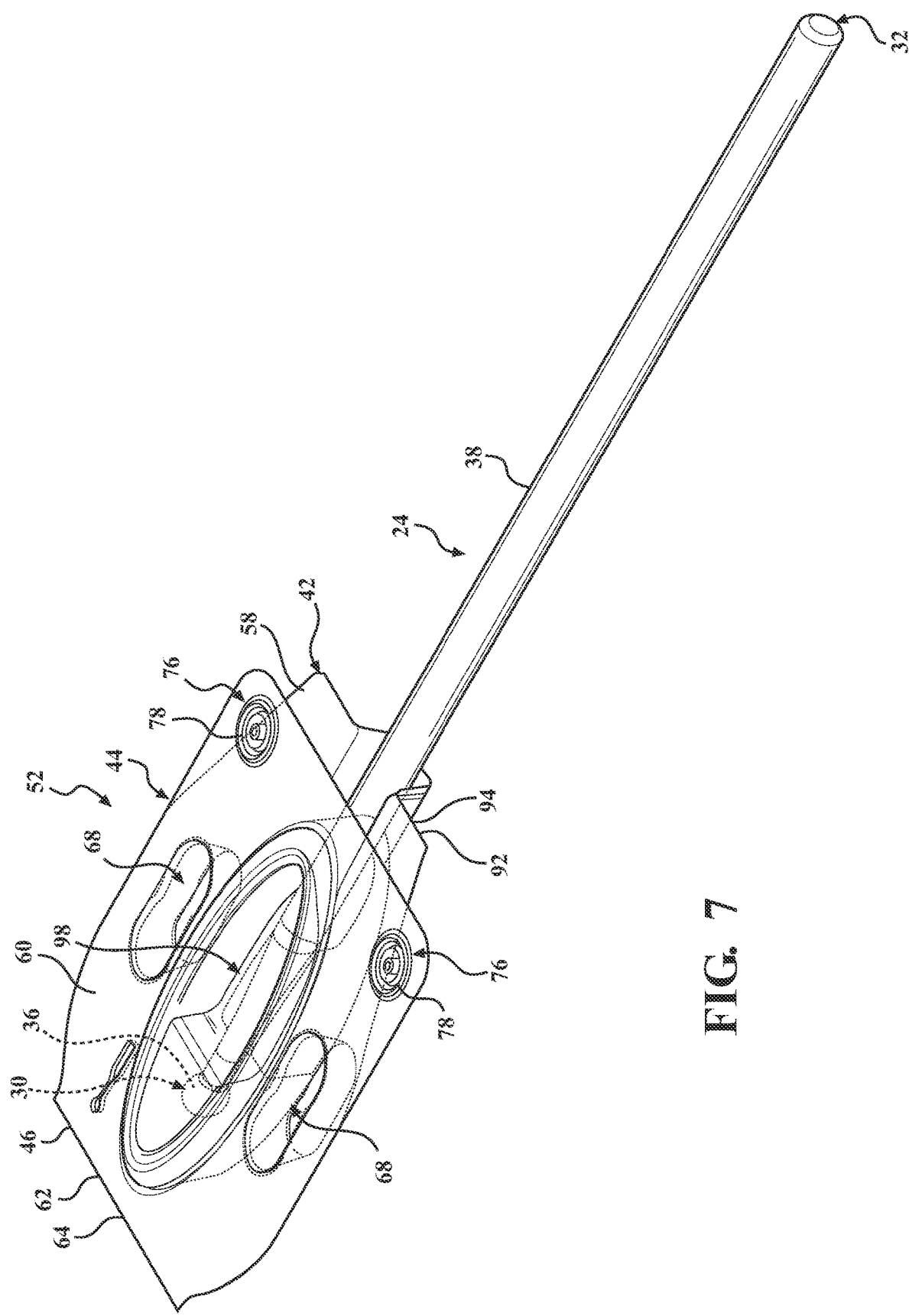
FIG. 7 is a perspective view of the packaging body of FIG. 3 with a proximal section detached from a distal section so as to expose a proximal portion of the elongate tool.

The first distal section 42 may be detachably coupled to the proximal section 50 at the proximal boundary 48. The packaging body 22 includes the perforation 94 at the proximal boundary 48 configured to facilitate detachment of the first distal section 42 from the proximal section 50, or vice versa. FIG. 7 shows the packaging body 22 subsequent to detachment of the proximal section 50 from the first distal section 42. The proximal section 50 may be detached from the first distal section 42 either prior to or after mounting or installing the tool 24 on the surgical device 28 in a manner to be described. The distal end 30 of the tool 24, including the head 36, may remain safely packaged in the casing 52 subsequent to detachment of the proximal section 50 from the first distal section 42.

To detach the proximal section 50 from the first distal section 42, the user may provide a force, through bending, pulling, rotating, or combination thereof, sufficient to tear along the perforations 94. The user may support the casing 52 with the opposing hand, or the tool 24 may be mounted on the surgical device 28 such that no user support may be necessary. Care should be taken to ensure that the force provided to detach the proximal section 50 from the first distal section 42 does not prematurely decouple the couplers 68 of the casing 52, unless intended by the user.

Figure 8:
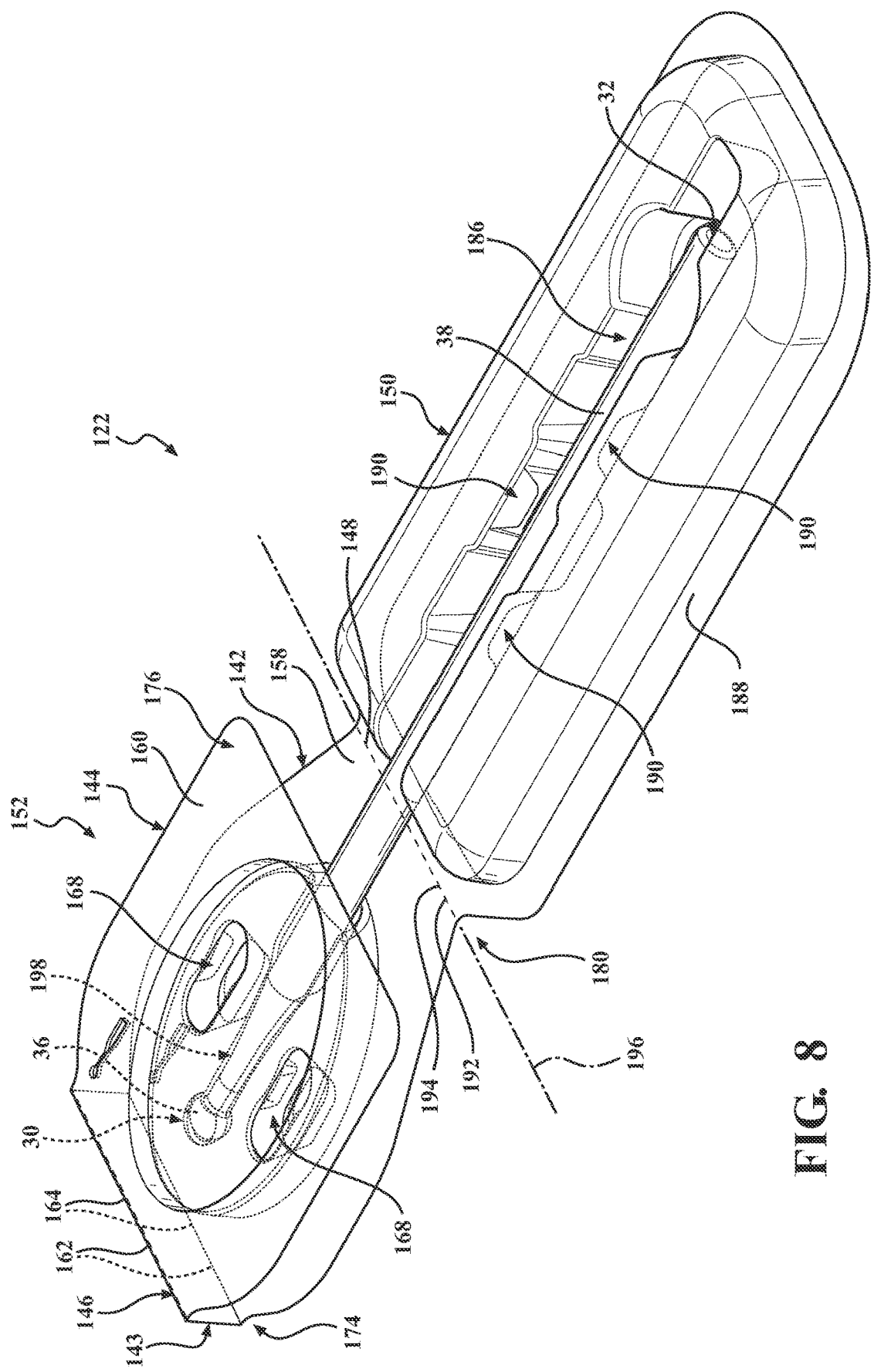
FIG. 8 is a packaging body in accordance with another example embodiment of the present disclosure with the elongate tool disposed within the packaging body in the first configuration.
Figure 9:
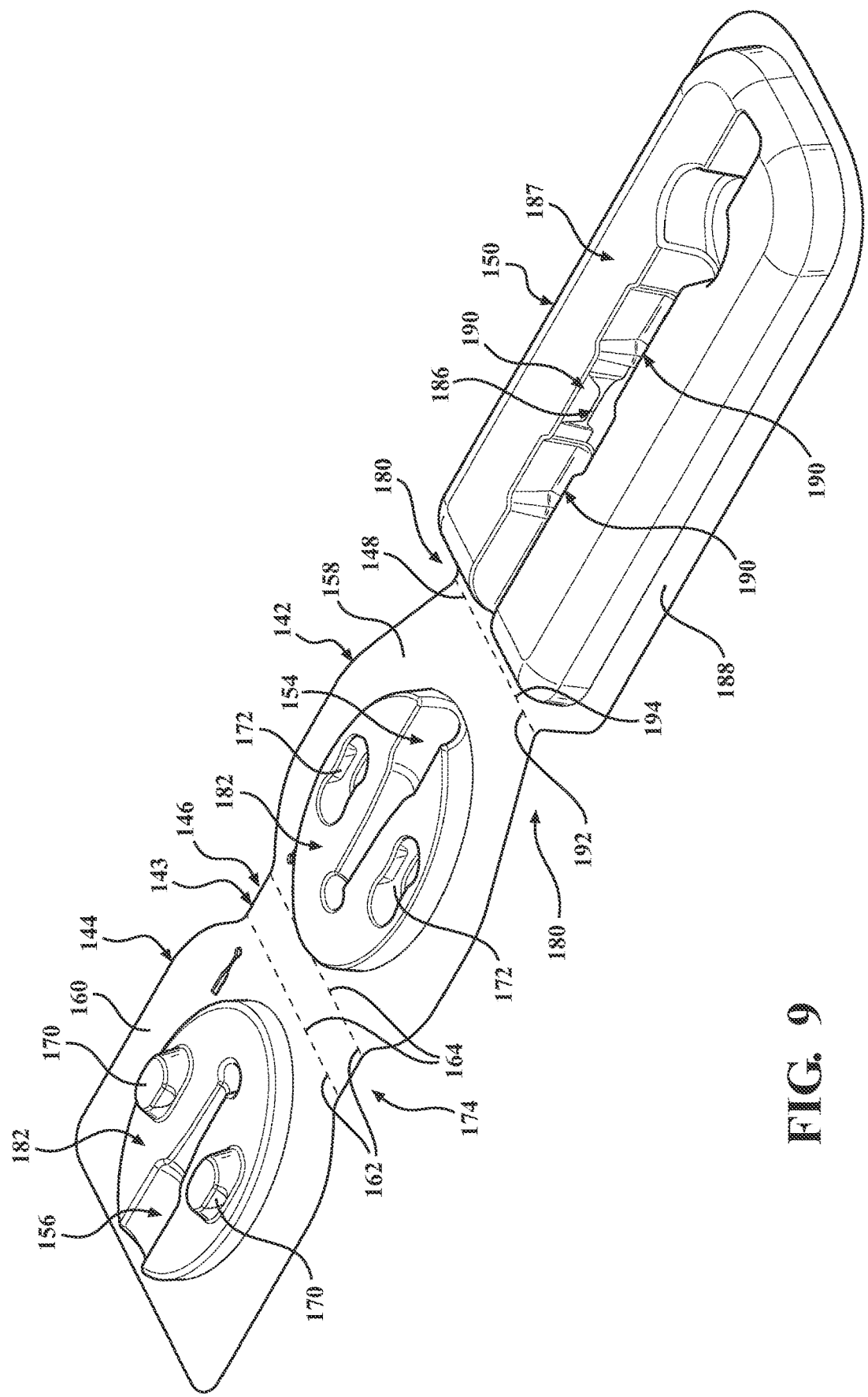
FIG. 9 is a perspective view of the packaging body of FIG. 8 in a second configuration with the elongate tool removed from the packaging body.
Figure 10:
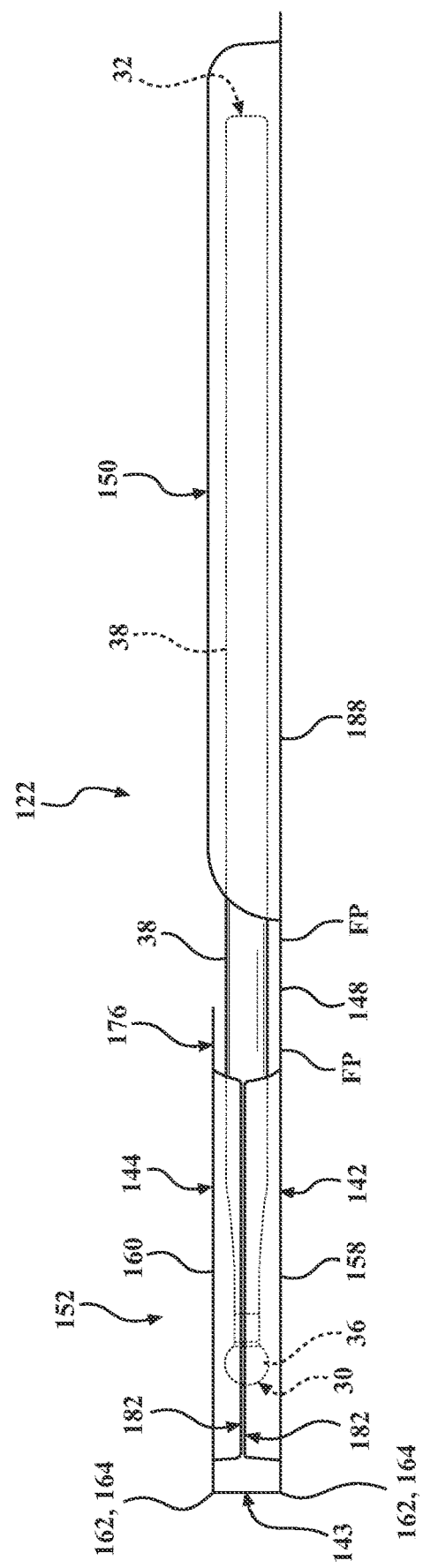
FIG. 10 is a side elevation view of the packaging body of FIG. 8 with the elongate tool disposed within the packaging body in the first configuration.

FIGS. 8-10 show a segmented packaging body 122 in accordance with another example embodiment of the packaging system 20. Like components of the packaging body 22 of the previously described embodiment are identified with a reference numeral increased by one hundred (100). Disclosure for the present embodiment of the packaging body 122 abbreviated from the previously described embodiment is not to be construed as limiting unless specifically indicated.

The packaging body 122 is configured to removably receive the elongate tool 24 configured to be mounted on the surgical device 28. Secondary packaging 26, such as the sealed pouch, the blister pack, or the like, may be provided and configured to receive the packaging body 122. The packaging body 122 includes the first distal section 142 and the second distal section 144. The first distal section 142 includes the distal boundary 146 and the proximal boundary 148. The second distal section 144 is coupled to the first distal section 142 at the distal boundary 146. The packaging body 122 further includes the proximal section 150 coupled to the first distal section 142 at the proximal boundary 148.

The packaging body 122 may further include a transition section 143 coupled to and positioned intermediate the first and second distal sections 142, 144. Based on the structure of the casing 152 of the present embodiment to be described, the transition section 143 provides spacing between the primary surfaces 158, 160 of the first and second distal sections 142, 144 such that, in the first configuration, the first and second distal sections 142, 144 are in the desired abutting relationship. The transition section 143 may define the distal boundary 146.

The transition section 143 may include two or more living hinges 162 separated by a surface. FIG. 8 shows the transition section 143 with two living hinges 162 such that, in the first configuration, the transition section 143 and first and second distal sections 142, 144 assume a substantially U-shaped configuration. The living hinges 162 may be described as a thin, flexible connection or web pivotally coupling each of the first and second distal sections 142, 144 with the transition section 143. Perforations 164 may be associated with each of the living hinges 162 such that the first distal section 142, the transition section 143, and/or the second distal section 144 are selectively detachable from one another.

The first and second distal sections 142, 144 are configured to receive the distal end 30 of the tool 24. FIG. 8 shows the first and second distal sections 142, 144 receiving the distal end 130 and a portion of the shaft 38 of the tool 24. The first and second distal sections 142, 144 may be pivotally coupled to provide the casing 152 to the distal end 30 of the tool 24.

The casing 52 may be provided by the cavity 154, 156 disposed in each of the first and second distal sections 142, 144. With reference to FIG. 9, the first distal section 142 includes the primary surface 158 extending between the distal boundary 146 and the proximal boundary 148. The second distal section 144 includes the primary surface 160. The primary surfaces 158, 160 may be considered as substantially flat portions of first and second distal sections 142, 144. Each of the first and second distal sections 142, 144 may include the boss 182 configured to support the tool 24 proximate the distal end 30. In the packaging body 122 of the present embodiment, the bosses 122 extend from the primary surfaces 158, 160 of the first and second distal sections 142, 144. The boss 182 include the cavities 154, 156 configured to receive the shaft 38 of the tool 24 proximal the head 36. The cavity 154, 156 may be substantially contoured to a distal region of the tool 24 such that, when the couplers 168 are coupled in the first configuration, the shaft 38 of the tool 24 proximal the head 36 is securely encased within the casing 152.

The cavities 154, 156 of each of the first and second distal sections 142, 144 may be in substantial alignment so as to receive the distal end 30 of the tool 24 in a first configuration. The casing 152 may be provided by articulating one of the first and second distal sections 142, 144 relative to the other between the first configuration shown in FIG. 8, and the second configuration shown in FIG. 9. The second distal section 144 may be pivotally coupled to the first distal section 142 at the distal boundary 146 comprising the living hinges 162 oriented perpendicular to the tool axis 34 of the tool 24. In the present embodiment, the boss 182 of each of the first and second distal sections 142, 144 are provided in a direct abutting relationship in the first configuration. With reference to FIG. 10, because the boss 182 of each of the first and second distal sections 142, 144 extend from the primary surfaces 158, 160 (with no cavity of the previously described embodiment), spacing is required between the primary surfaces 158, 160 to directly abut the bosses 182 in a flat-on-flat manner. The transition region 143 is suitably sized to provide the spacing required to achieve the direct abutting relationship shown in FIGS. 8 and 10. The primary surfaces 158, 160 of the first and second distal sections 142, 144 may be substantially parallel in the first configuration. The first and second distal sections 142, 144 are positioned in a non-abutting relationship in the second configuration as shown in FIG. 9 (with the tool 24 removed).

The packaging body 122 further includes the couplers 168 removably coupling the first and second distal sections 142, 144. The couplers 168 are configured to maintain the first and second distal sections 142, 144 in the first configuration absent the input from the user. In certain embodiments, the couplers 168 include the protrusion 170 removably coupled to the recess 172 by interference fit in the first configuration. The recess 172 may be provided within the boss 182 of one of the first and second distal sections 142, 144, and the protrusion 170 provided within the boss 182 on the other one of the first and second distal sections 142, 144. In the example embodiment shown in FIGS. 8 and 9, two recesses 172 and two protrusions 170 are provided. The protrusions 170 and recesses 172 are positioned on opposing sides of the cavities 154, 156 of the boss 182 of each of the first and second distal sections 142, 144. The interference fit between the protrusion 170 and the recess 172 maintains the casing 152 such that the first and second distal sections 142, 144 encase the distal end 30 of the tool 24.

Moving the packaging body 122 from the first configuration to the second configuration includes pivoting one of the first and second distal sections 142, 144 about the distal boundary 146 comprising the living hinges 162 oriented transverse to the tool axis 34. The desired movement may be further facilitated by the cutouts 174 comprising material removed or absent from one or more of the first and second distal sections 142, 144 at the opposing ends of the living hinges 162, as shown in FIGS. 8 and 9. In the second configuration, the cutouts 174 may be trapezoidal when viewed in plan, but other suitable shapes are contemplated. The cutouts 174 may localize stresses in a suitable manner to facilitate relative pivoting of first and second distal sections 142, 144 relative to the transition section 143 and one another.

The relative pivoting is typically imparted by the user holding the packaging body 122. In one example, the user may hold the proximal section 150 and/or the first distal section 142 in one hand and grasp the second distal section 144 with the other hand in order to overcome the interference fit of the couplers 168. The user may use fingers to pinch or grasp the second distal section 144 while holding of the first distal section 142. The spacing between the primary surfaces 158, 160 may provide clearance for the user to pinch or grasp the primary surface 160 of the second distal section 144. The packaging body 22 may further include the finger grip 176 comprising a portion of the primary surface 160 of the second distal section 144 extending outwardly from the first distal section 142. The finger grip 176 may be positioned adjacent and/or proximate to the cutouts 180 associated with the proximal boundary 148.

The packaging body 122 includes the proximal section 150 coupled to the first distal section 142 at the proximal boundary 148. The proximal section 150 may further include the primary surface 188 coupled to the primary surface 158 of the first distal section 142 at the proximal boundary 148. The proximal section 150 is configured to receive a proximal portion of the shaft 38 of the tool 24 comprising the proximal end 32.

The proximal section 150 includes the cavity 186 configured to receive the proximal portion of the tool 24. The cavity 186 may be provided within a proximal shelf 187. The proximal shelf 187 extends from the primary surface 188 of the proximal section 150 and defines the cavity 186. The proximal shelf 187 defining the cavity 186 is suitably sized such that the cavity 186 of the proximal section 150 and the cavity 154 of the first distal section 142 are aligned (e.g., substantially collinear). FIG. 9 shows the cavity 186 is elongate and suitably sized to receive the tool 24. The tool 24 may be secured within the cavity 186 with the one or more shaft couplers 190 which include, for example, the protrusions with the counterposing recesses to provide the interference fit to the shaft 38 of the tool 24. The interference fit may be provided by a small amount of elastic deformation of the shaft coupler 190 that occurs as the tool 24 is urged within the cavity 186 of the proximal section 150.

The cavity 154 of the first distal section 142 and the cavity 186 of the proximal section 150 may be separated by flat portions of the first distal section 142 and the proximal section 150. Referring to FIGS. 8-10, the flat portion of the first distal section 142 may be defined as the primary surface 158 intermediate the boss 182 and the proximal boundary 148 (see FP of FIG. 10). The flat portion of the proximal section 152 may be defined as the primary surface 188 intermediate the proximal shelf 187 and the proximal boundary 148. The flat portions provide for, among other things, the proximal boundary 148 being linear. Consequently, the living hinge 192 and the perforations 194 at the proximal boundary 148 are linear. The living hinge 192 being linear may facilitate easier relative pivoting between the first distal section 142 and the proximal section 150 with greater magnitudes of articulation. The perforation 194 being linear may facilitate easier detachment of the proximal section 150 from the first distal section 142 relative to more complex geometries.

The proximal section 150 is configured to move between the packaging configuration and the installation configuration. The packaging configuration, as shown in FIG. 8, includes the proximal end 32 of the tool 24 disposed within the cavity 186 of the proximal section 150. In the packaging configuration, the primary surfaces 158, 188 of the first distal section 142 and the proximal section 150 may be substantially coplanar. The flat portions may result in a portion of the shaft 38 of the tool 24 being exposed in the packaging configuration, as shown in FIG. 10. FIG. 8 also shows the first and second distal sections 142, 144 in the first configuration; e.g., the boss 182 of the first and second distal sections 142, 144 are positioned in an abutting relationship. In the first configuration, the primary surfaces 158, 160 of the first and second distal sections 142, 144 may be substantially parallel.

The installation configuration includes pivoting the proximal section 150 relative to the first distal section 142, thereby exposing the proximal end 32 of the tool 24 outside the cavity 186 of the proximal section 150. The proximal section 150 may be configured to be moved from the packaging configuration to the installation configuration while the first and second distal sections 142, 144 are in the first configuration. The living hinge 192 and the cutouts 180 facilitate the relative pivoting between the first distal section 142 and the proximal section 150 at the proximal boundary 148. The living hinge 192 may be oriented on the axis 196 (see FIG. 8) perpendicular to the tool axis 34 of the tool 24, and parallel to the living hinges 162 at the distal boundary 146. The cutouts 180 may include material removed or absent from one or more of the first distal section 142 and the proximal section 150 at the opposing ends of the proximal boundary 148. The tool 24 may be mounted on the surgical device 28 while the packaging body 122 is in the installation configuration as to be described.

The first distal section 142 may be detachably coupled to the proximal section 150 at the proximal boundary 148. The packaging body 122 includes the perforations 194 at the proximal boundary 148 configured to facilitate detachment of the first distal section 142 from the proximal section 150, or vice versa. To detach the proximal section 150 from the first distal section 142, the user may provide a force, through bending, pulling, rotating, or combination thereof, sufficient to tear along the perforations 194. The proximal section 150 may be detached from the first distal section 142 after mounting or installing the tool 24 on the surgical device 28. The distal end 30 of the tool 24, including the head 36, may remain safely packaged in the casing 152 subsequent to detachment of the proximal section 150 from the first distal section 142.

Example methods of mounting the elongate tool 24 on the surgical device 28 are also disclosed. FIG. 11 shows the robot R having an end effector EE, which includes a non-limiting example of the surgical device 28. It is to be understood the methods described herein may be applicable to any number and type of tools and surgical devices, and the surgical device 28 need not include the robot R and/or the end effector EE. In certain embodiments, the packaging system 20 and example methods may be utilized to mount the tool 24 to a handheld powered surgical device such as a bone drill, oscillating saw, and the like. In other embodiments, the tool 24 may be mounted to a handheld and non-powered surgical device such as a scalpel, an endoscope, and the like. The tool 24 need not include a cutting accessory with sharp features. Further, the example methods of mounting the tool 24 may not require that the tool 24 need be sterilized. FIGS. 13-22 show a representative example of the end effector EE to describe the methods of mounting the tool 24 on the surgical device 28, and the representative example should not be construed as limiting.

The tool 24 includes the distal end 30 opposite the proximal end 32. The method may include providing the distal end 30 of the tool 24 within a distal cavity defined between the first distal section 42, 142 and the second distal section 44, 144. In certain embodiments, the distal cavity may be defined as the combination of the cavity 54, 154 of the first distal section 42, 142 and the cavity 56, 156 of the second distal section 44, 144. The distal cavity is referenced in FIGS. 3 and 7 as reference numeral 98 and in FIG. 8 as reference numeral 198.

Figure 12:
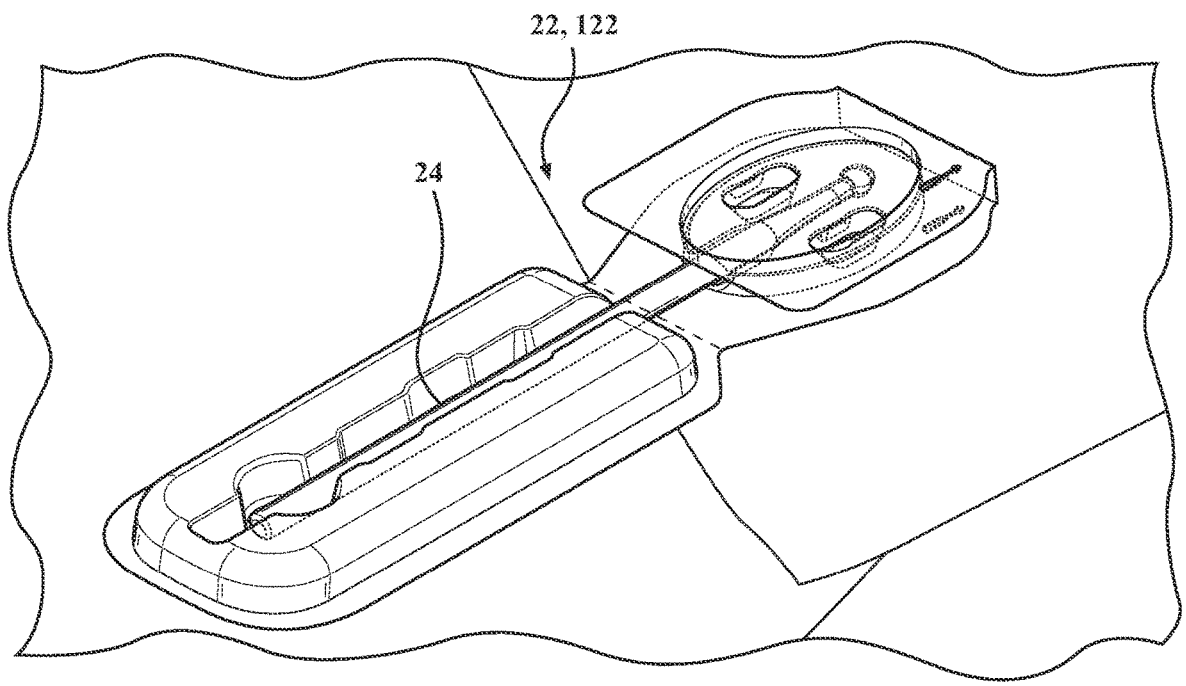
FIG. 12 shows a step of an example method of mounting the elongate tool on the surgical device.

Referring to FIG. 12, the tool 24 is disposed within the segmented packaging body 22, 122. FIGS. 12-22 show the packaging body 122 of the embodiment illustrated in FIGS. 8-10. It is to be understood the example methods may be similarly performed with the embodiment illustrated in FIGS. 1-7. The packaging body 22, 122 including the tool 24 is initially positioned away from the end effector EE. The packaging body 22, 122 may be disposed with secondary packaging 26 such as the sealed pouch or the blister pack. Example methods may include removing the packaging body 22, 122 from the secondary packaging 26.

With concurrent reference to FIGS. 3 and 8, FIG. 12 shows the packaging body 22, 122 in the first configuration and the packaging configuration. The first configuration includes the first distal section 42, 142 and the second distal section 44, 144 positioned in the abutting relationship such that the distal end 30 of the tool 24 is encased in the casing 52, 152. In the first configuration, the distal end 30 of the tool 24 is disposed within the cavity 54, 154 of the first distal section 42, 142 and the proximal end 32 of the tool 24 is disposed within the cavity 86, 186 of the proximal section 50, 150. The primary surface 58, 158 of the first distal section 42, 142 and the primary surface 60, 160 of the second distal section 44, 144 may be substantially parallel in the first configuration. The packaging configuration includes the proximal end 32 of the tool 24 disposed within the cavity 86, 186 of the proximal section 50, 150. The primary surface 58, 158 of the first distal section 42, 142 and the primary surface 88, 188 of the proximal section 50, 150 may be substantially coplanar in the packaging configuration. The packaging configuration may further be associated with the packaging body 22, 122, being in the first configuration as reflected in FIGS. 3, 8 and 12.

Figure 13:
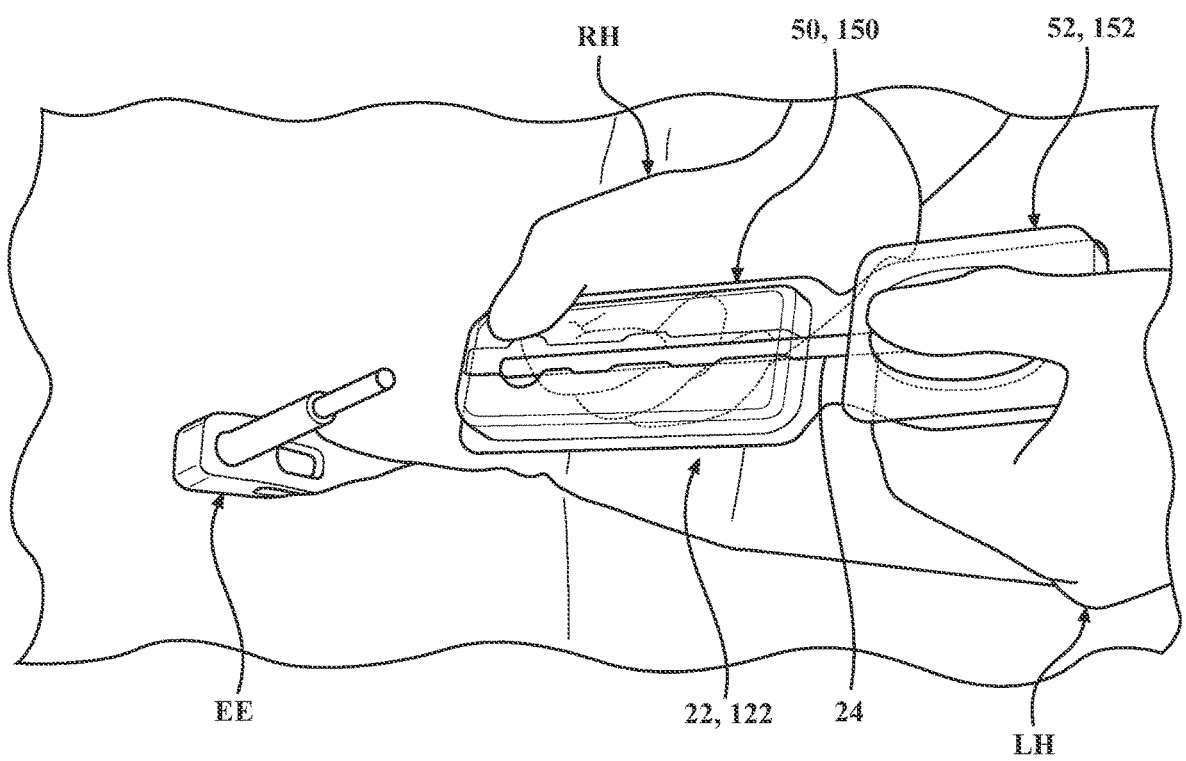
FIG. 13 shows another step of the example method of mounting the elongate tool on the surgical device.
Figure 14:
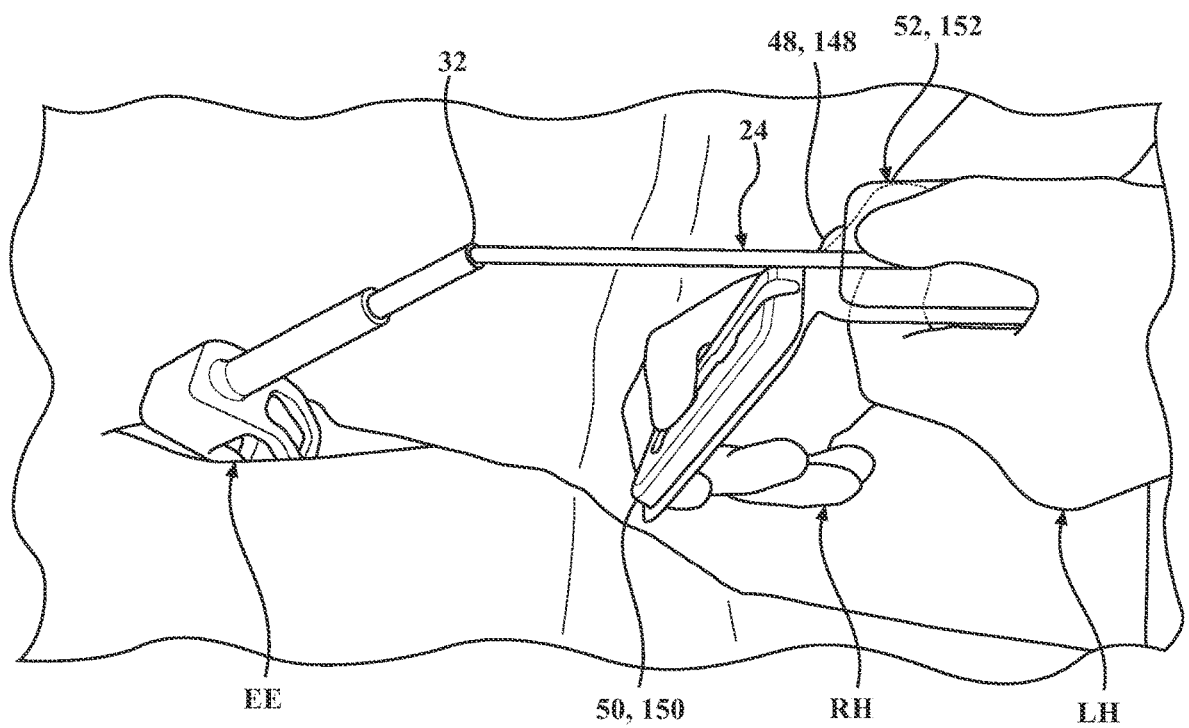
FIG. 14 shows another step of the example method of mounting the elongate tool on the surgical device.

The user grasps the packaging body 22, 122 with, for example, the right hand RH and the left hand LH as shown in FIG. 13. Since the proximal end 32 of the tool 24 is to be mounted on the end effector EE, the user may grasp the packaging body 22, 122 by the casing 52, 152 with the proximal section 50, 150 of the packaging body 22, 122 oriented towards the end effector EE. FIG. 13 shows the user grasping the casing 52, 152 with the left hand LH and the proximal section 50, 150 with the right hand RH. While holding the packaging body 22, 122, the method includes articulating the proximal section 50, 150 about the proximal boundary 48, 148 relative to the first distal section 42, 142 to remove the proximal end 32 of the tool 24 from the cavity 86, 186 of the proximal section 50, 150. FIG. 14 shows the user articulating the proximal section 50, 150 with the right hand RH while supporting the casing 52, 152 with the left hand LH. The user may pinch between a thumb and index finger the casing 52, 152 so as to maintain the casing 52, 152 in the first configuration and avoid inadvertent decoupling of the first distal section 42, 142 and the second distal section 44, 144. The relative articulation exposes the proximal end 32 of the tool 24.

The relative articulation may be imparted by the left hand LH of the user. The proximal section 50, 150 may pivot about the living hinge 92, 192 at the proximal boundary 48, 148, and the cutouts 80, 180 may facilitate the pivoting. The pivoting of the proximal section 50, 150 relative to the first distal section 42, 142 to expose the proximal end 32 of the tool 24 includes moving the packaging body 22, 122 from the packaging configuration to the installation configuration.

Figure 15:
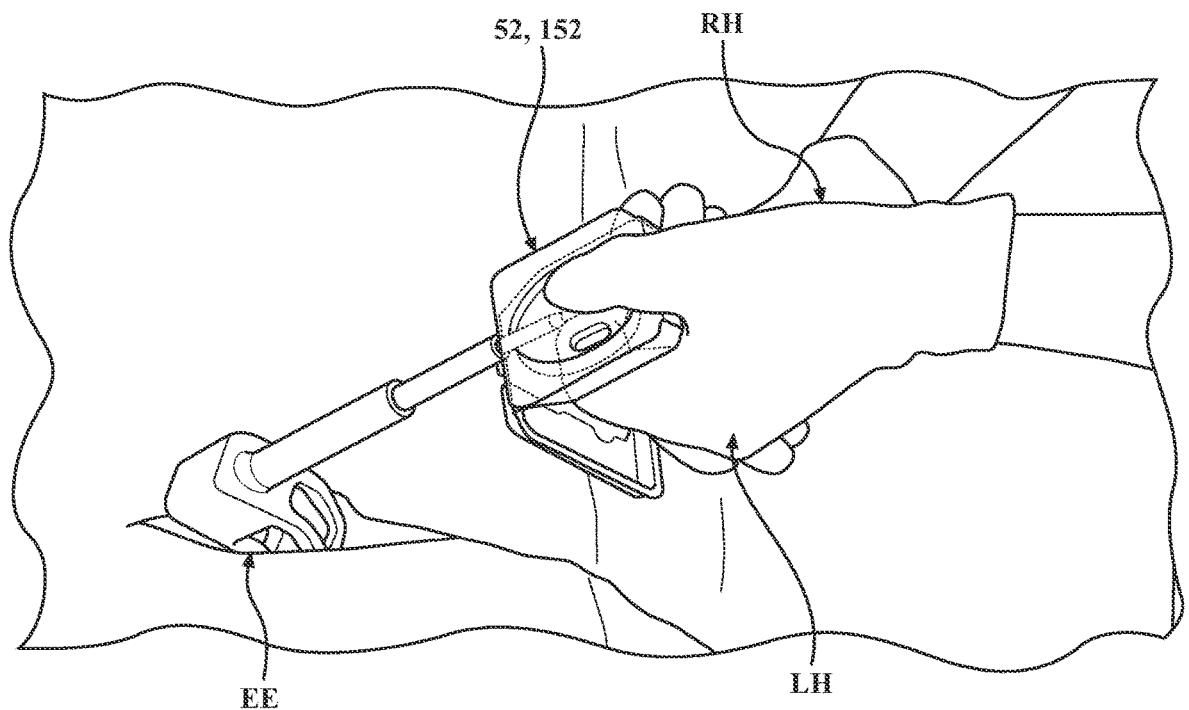
FIG. 15 shows another step of the example method of mounting the elongate tool on the surgical device.

Referring to FIGS. 14 and 15, the proximal end 32 of the tool 24 is mounted on the surgical device 28 while the distal end 30 of the tool 24 remains disposed within the distal cavity 98, 198 in the casing 52, 152. In other words, the tool 24 is installed while the packaging body 22, 122 is in the first configuration and the installation configuration. FIG. 14 shows the step of mounting includes inserting the proximal end 32 of the tool 24 within the end effector EE. The packaging body 22, 122 is configured to be grasped by the user when the tool 24 is mounted on the surgical device 28 while the packaging body 22, 122 is in the installation configuration as to avoid user contact with the tool 24. FIG. 15 shows the user slidably moving the tool 24 into a desired engagement with the end effector EE while supporting the packaging body 22, 122. The user is supporting the casing 52, 152 with the left hand LH and the proximal section 50, 150 with the right hand RH as the shaft 38 of the tool 24 is slidably received with the end effector EE.

After mounting the proximal end 32 of the tool 24 on the surgical device 28, the method may further include the step of detaching the proximal section 50, 150 from the first distal section 42, 142 at the proximal boundary 48, 148. The proximal boundary 48, 148 includes the perforations 94, 194 to facilitate detaching the proximal section 50, 150 from the first distal section 42, 142 at the perforations 94, 194. Subsequent to detachment of the proximal section 50, 150, the remainder of the packaging body 22, 122 assumes the configuration shown in FIG. 18.

Figure 16:
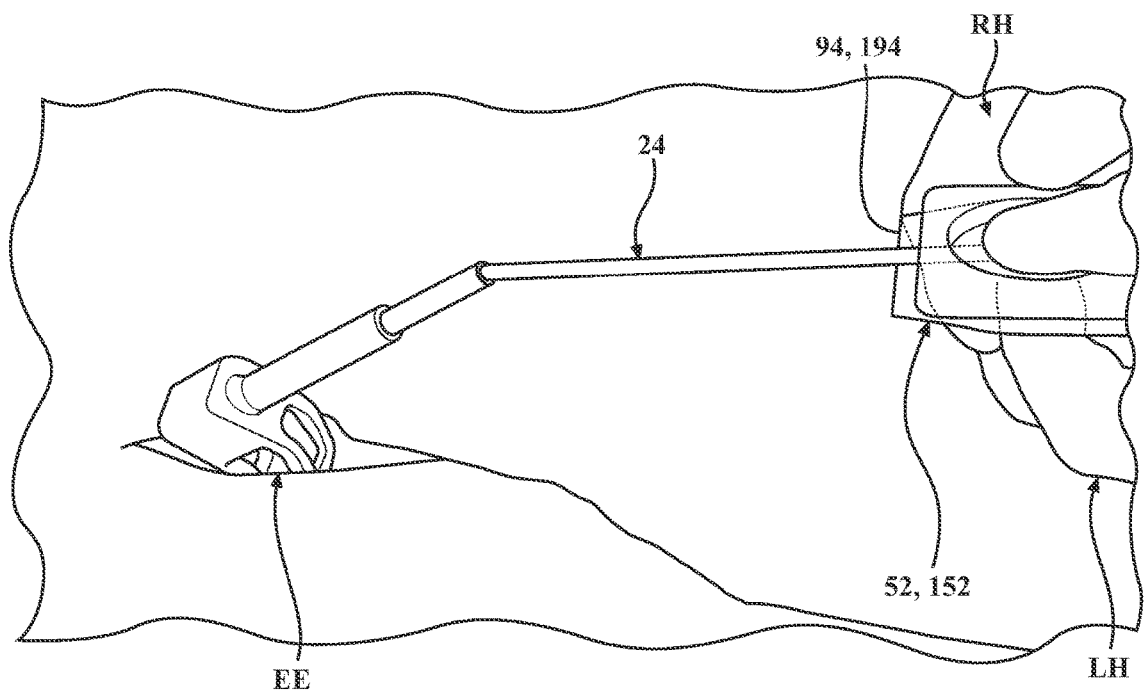
FIG. 16 shows another step of the example method of mounting the elongate tool on the surgical device.
Figure 17:
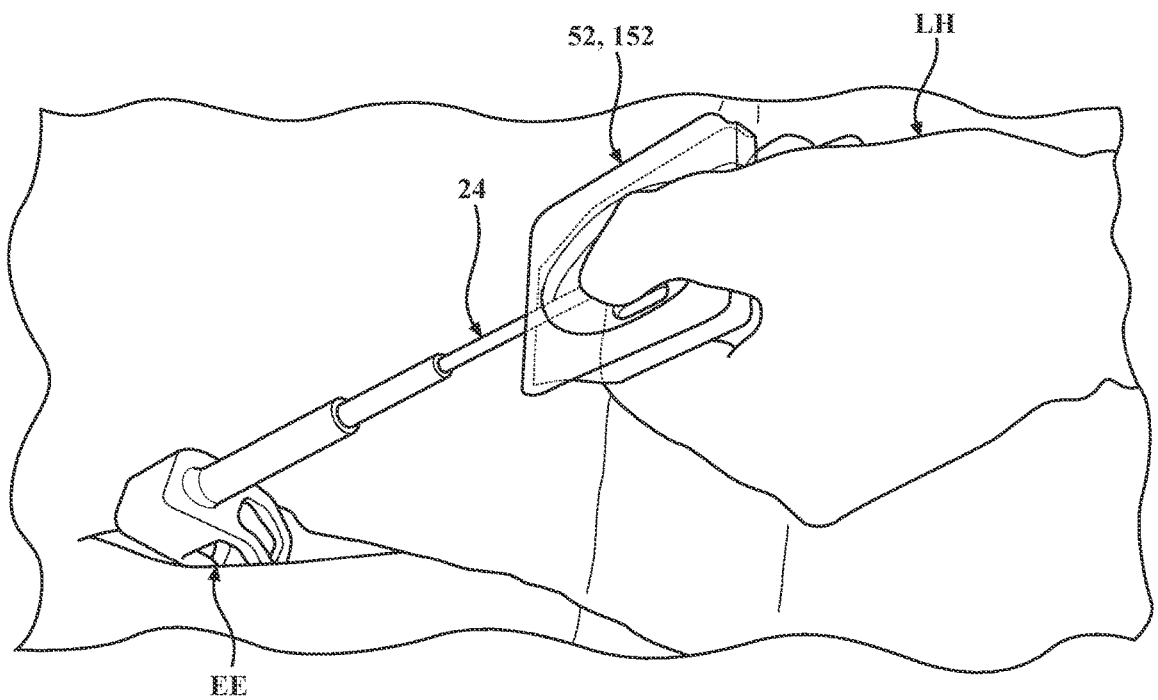
FIG. 17 shows another step of the example method of mounting the elongate tool on the surgical device.
Figure 18:
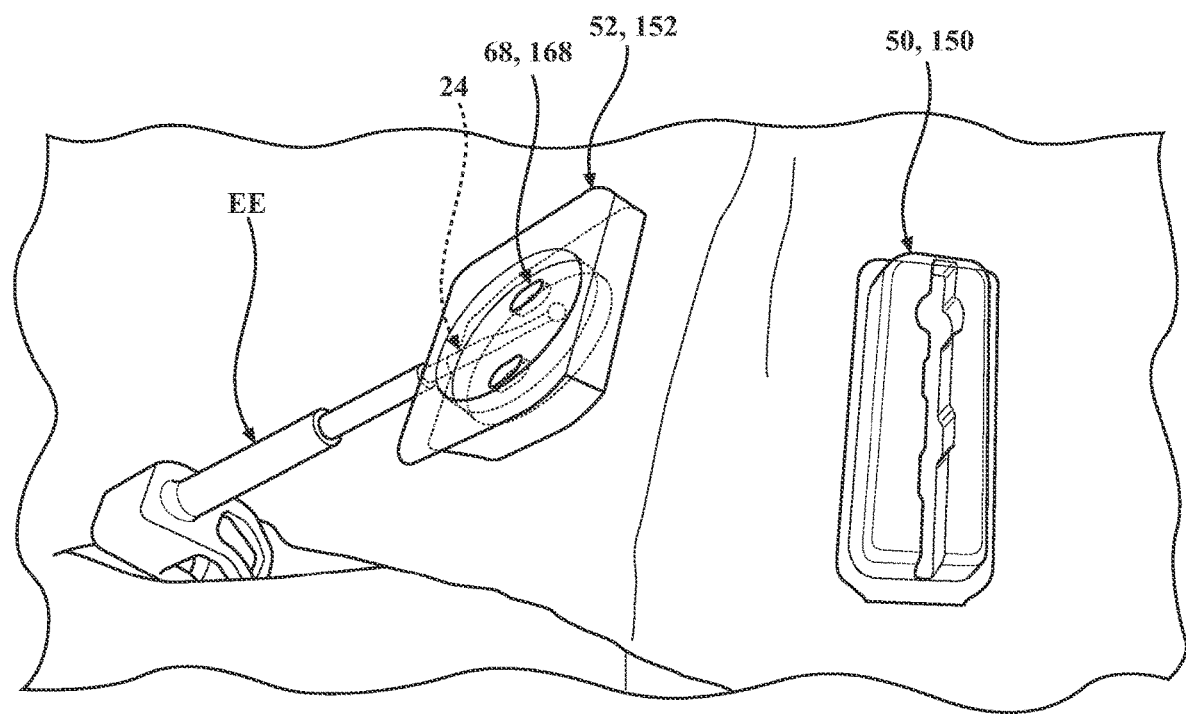
FIG. 18 shows another step of the example method of mounting the elongate tool on the surgical device.

In another example method, the proximal section 50, 150 may be detached from the first distal section 42, 142 prior to mounting or installing the tool 24 on the surgical device 28. Referring to FIGS. 16 and 17, the casing 52, 152 is shown without the proximal section 50, 150. The user detaches the proximal section 50, 150 from the first distal section 42, 142 at the perforations 94, 194. With one or both of the right hand RH and the left hand LH, the user mounts the proximal end 32 of the tool 24 on the surgical device 28. FIG. 16 shows the user supporting the casing 52, 152 with both the right hand RH and the left LH, and FIG. 17 shows the user supporting the casing 52, 152 with the left hand LH. The user may remove one of the hands RH, LH after a portion of the shaft 38 of the tool 24 is confidently within the end effector EE such that suitable engagement is ensured. The right hand RH of the user is now free to perform any other number of tasks related or unrelated to mounting the tool 24 on the surgical device 28. The packaging body 22, 122 assumes the configuration shown in FIG. 18.

Figure 19:
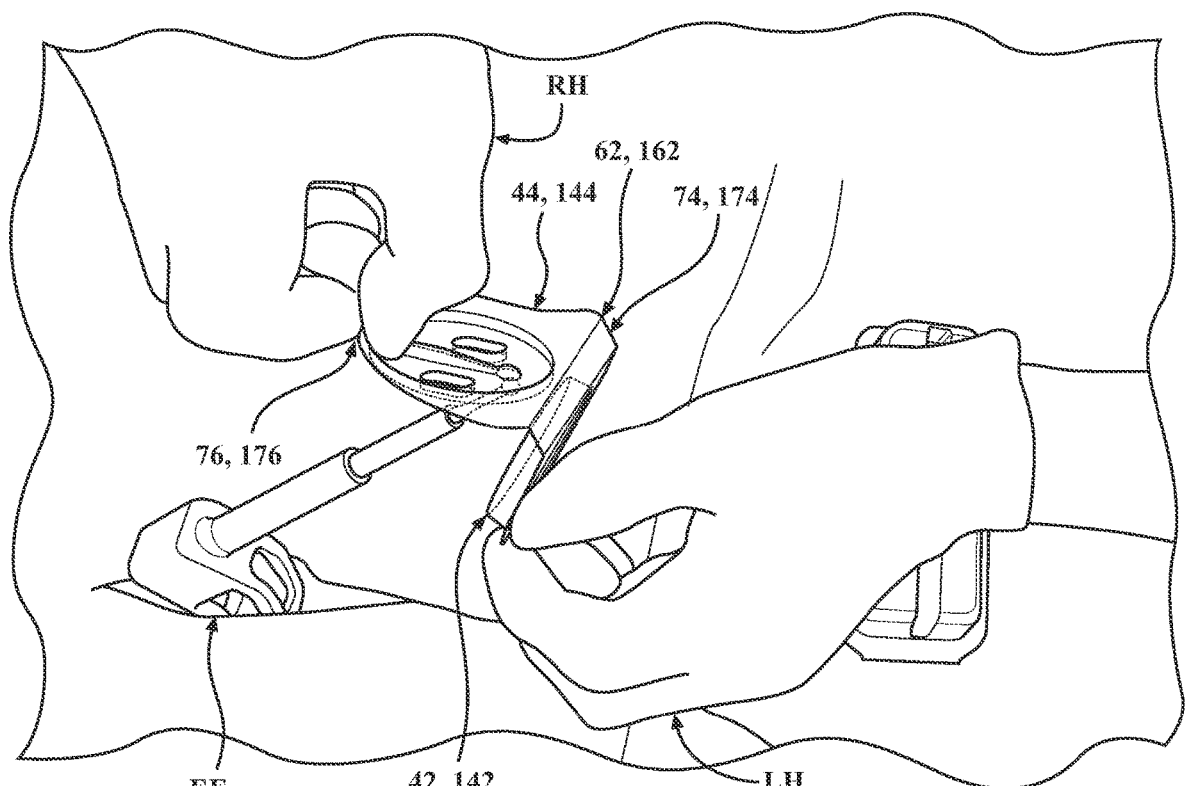
FIG. 19 shows another step of the example method of mounting the elongate tool on the surgical device.
Figure 20:
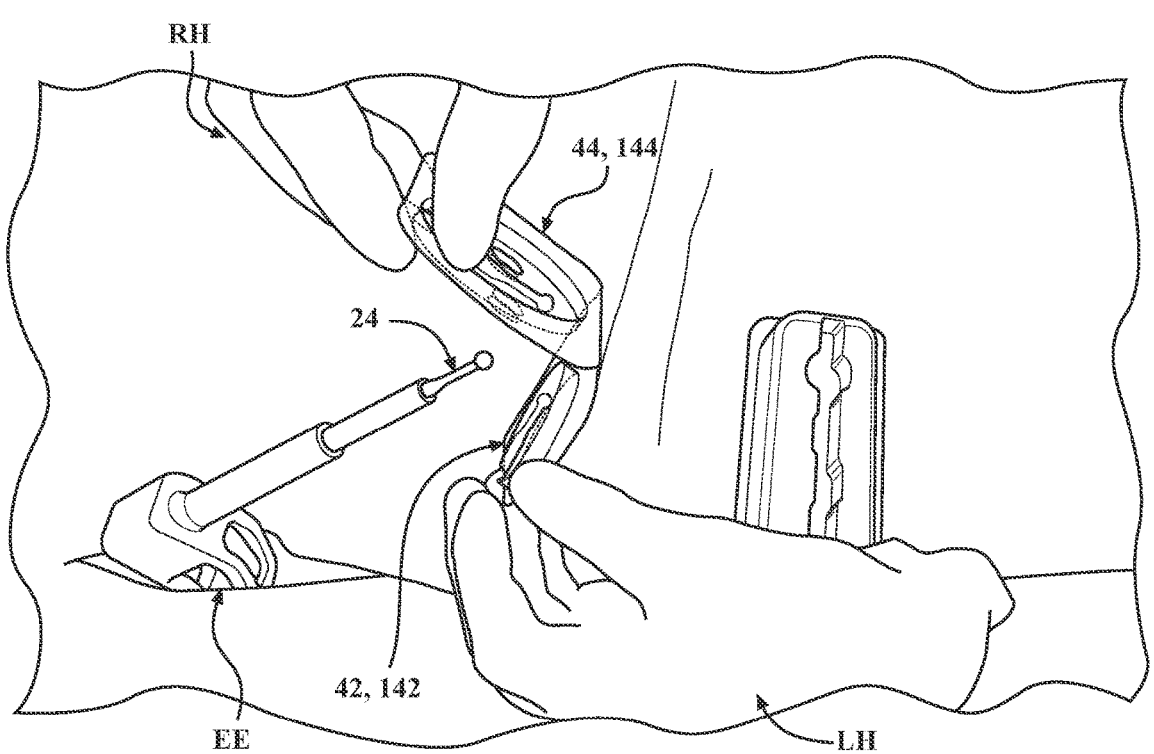
FIG. 20 shows another step of the example method of mounting the elongate tool on the surgical device.
Figure 21:
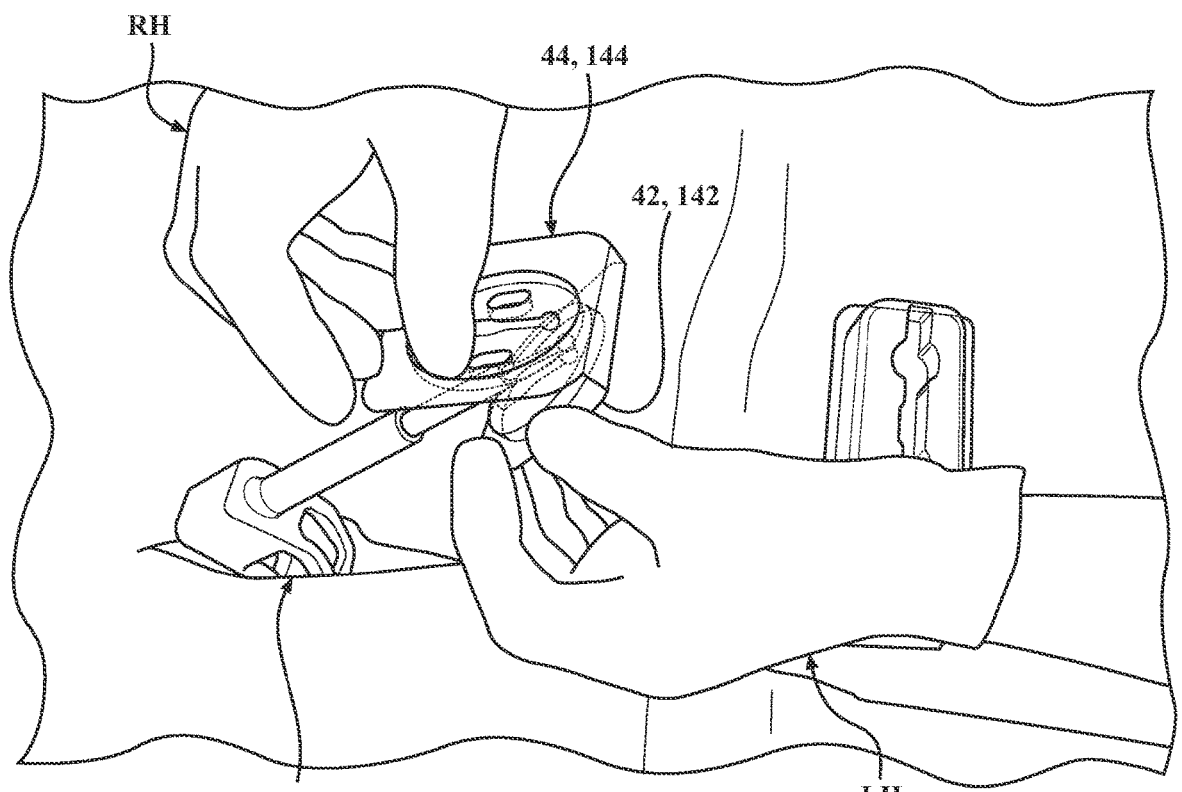
FIG. 21 shows a step of coupling a casing of the packaging body to the elongate tool.

In certain embodiments, the method further includes articulating one of the first distal section 42, 142 and the second distal section 44, 144 about the distal boundary 46, 146 relative to the other to expose at least a portion of the distal end 30 of the tool 24. FIGS. 19 and 20 show the user moving the packaging body 22, 122 from the first configuration to the second configuration. In the second configuration, the first distal section 42, 142 and the second distal section 44, 144 are in a non-abutting relationship. Stated simply, the user is opening the casing 52, 152 encasing the distal end 30 of the tool 24. In the illustrative embodiment of FIG. 16, the proximal section 50, 150 is no longer coupled to the first distal section 42, 142 before the packaging body 22, 122 is moved from the first configuration to the second configuration.

To articulate one of the first distal section 42, 142 and the second distal section 44, 144 about the distal boundary 46, 146, the user may grasp the first distal section 42, 142 and pinch or grasp a portion of the second distal section 44, 144, such as with the finger grips 76, 176. The step of articulating may further include decoupling the couplers 68, 168. The force applied by the user to the second distal section 44, 144 overcomes the interference fit provided by the couplers 68, 168 (see FIG. 18). The living hinge 62, 162 and/or the cutouts 74, 174 facilitate the relative pivoting between the first distal section 42, 142 and the second distal section 44, 144 at the distal boundary 46, 146. The user removes the other one of the first distal section 42, 142 and the second distal section 44, 144 from the distal end 30 of the tool 24. The user removes the packaging body 22, 122 from the head 36 of the tool 24 with sufficient clearance to avoid contamination. The head 36 of the tool 24 is now exposed and ready for use during a surgical procedure. It is to be appreciated that the user has not touched the tool 24 in any significant manner, and the head 36 of the tool 24 was shielded from contamination.

In another example method, the user may wish to delay between the step of mounting the tool 24 on the surgical device 28 and/or removing the packaging body 22, 122 to expose the distal end 30 of the tool 24. For example, an operating room technician may mount the tool 24 on the end effector EE well in advance of the surgical procedure. For any desired amount of time, the packaging body 22, 122 may remain in the configuration shown in FIG. 18. The remainder of the packaging body 22, 122 is in the first configuration such that the first distal section 42, 142 and the second distal section 44, 144 are in the abutting relationship. The head 36 of the tool 24 remains secured and protected within the casing 52, 152 after the tool 24 is mounted on the surgical device 28. Should inadvertent contact occur with the tool 24, the risk of contamination and/or injury to the user and/or surgical device 28 is greatly reduced.

Once desired, the casing 52, 152 may be removed from the tool 24 to expose the distal end 30 of the tool 24. After the step of detaching the proximal section 50, 150 from the first distal section 42, 142, one of the first distal section 42, 142 and the second distal section 44, 144 is articulated relative to one another about the distal boundary 46, 146 to expose the distal end 30 as described. In the illustrative embodiment shown in FIGS. 19 and 20, the user may grasp the first distal section 42, 142 with the left hand LH and the second distal section 44, 144 with the right hand RH. The casing 52, 152 is sufficiently opened and the user removes the remainder of the packaging body 22, 122 from the head 36 of the tool 24 with sufficient clearance to avoid contamination. The head 36 of the tool 24 is now exposed and ready for use.

At any point prior to, during, and/or after the surgical procedure, the casing 52, 152 may be reattached to the tool 24 so as to secure and protect the head 36 of the tool 24 within the casing 52, 152. In one example, the tool 24 may need to be removed from the surgical device 28 and/or mounted to another surgical device 28. In another example, an intermediate portion of the surgical procedure may not require the tool 24, during which the tool 24 is protected from inadvertent contact and/or contamination. In still another example, an earlier portion of the surgical procedure requiring the tool 24 has been completed, and the tool 24 is protected for the remainder of the procedure, or discarded. Any number of reasons for reattaching the casing 52, 152 to the tool 24 are contemplated.

Figure 22:
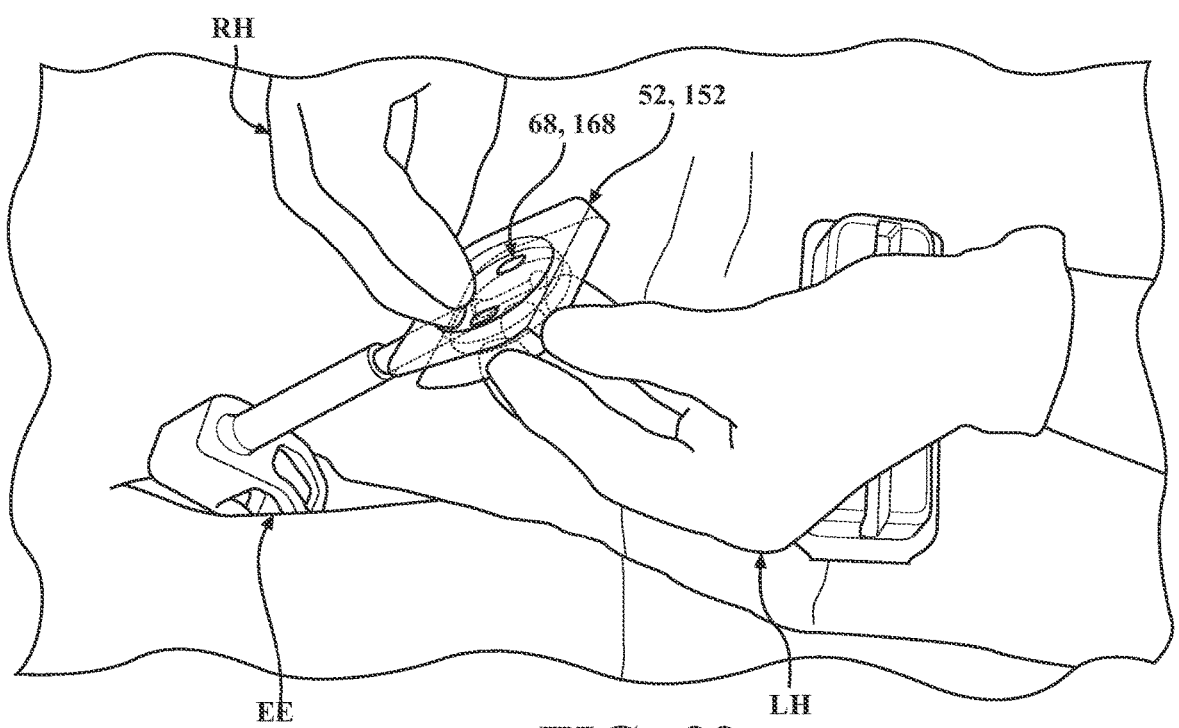
FIG. 22 shows another step of coupling the casing of the packaging body to the elongate tool.

The method may further include the step of moving the casing 52, 152 from the second configuration to the first configuration, such as after it had previously been removed from the distal end 30 of the tool 24. The method may further include the step of articulating one of the first distal section 42, 142 and second distal section 44, 144 about the distal boundary 46, 146 relative to the other one of the first distal section 42, 142 and second distal section 44, 144 to prevent exposure of at least a portion of the distal end 30 of the tool 24. With FIGS. 21 and 22 as example, the user supports the first distal section 42, 142 with the left hand LH and the second distal section 44, 144 with the right hand RH. The user moves the casing 52, 152 proximate the distal end 30 of the tool 24 with the first distal section 42, 142 and the second distal section 44, 144 positioned on opposite sides of the tool 24. The relative articulation between the first distal section 42, 142 and the second distal section 44, 144 is imparted by the user to move the first distal section 42, 142 and the second distal section 44, 144 towards one another. The distal end 30 of the tool 24 is received in one or both of the cavities 54, 56, 154, 156. FIG. 22 shows the user applying a compressive force to the first distal section 42, 142 and the second distal section 44, 144 to engage the couplers 68, 168. The interference fit generated by the engagement of the couplers 68, 168 causes the casing 52 to securely encase the distal end 30 of the tool 24. The packaging body 22, 122 reassumes the configuration shown in FIG. 18. It is to be understood that the casing 52, 152 may be decoupled and coupled to the tool 24 as many times as needed prior to, during, and after surgical procedure.

Example methods of assembling the packaging system 20 of the present disclosure are disclosed. The packaging body 22, 122 may be manufactured by thermoforming or another suitable manufacturing process. With reference to FIG. 5, following manufacture the first distal section 42, 142 and second distal section 44, 144 may be positioned in a non-abutting relationship with the primary surface 58, 158 of the second distal section 44, 144 and the primary surface 88, 188 of the proximal section 50, 150 coplanar.

The method further includes the step of inserting the tool 24 into the packaging body 22, 122. The tool 24 is disposed within the cavity 54, 154 of the first distal section 42, 142 and the cavity 86, 186 of the proximal section 50, 150. More specifically, the distal end 30 of the tool 24, including the head 36, is disposed within the cavity 54, 154 of the first distal section 42, 142, and the shaft 38 of the tool 24, including the proximal end 32, is disposed within the cavity 86, 186 of the proximal section 50, 150. The packaging body 22, 122, assumes the second configuration and the packaging configuration as described. More specifically, the first distal section 42, 142 and second distal section 44, 144 are positioned in a non-abutting relationship, thereby exposing a portion of the distal end 30 of the tool 24, and the proximal end 32 of the tool 24 is disposed within the cavity 86, 186 of the proximal section 50, 150.

The casing 52, 152 may be moved from the second configuration to the first configuration. The method may further include the step of articulating one of the first distal section 42, 142 and second distal section 44, 144 about the distal boundary 46, 146 relative to the other one of the first distal section 42, 142 and second distal section 44, 144 to prevent exposure at least a portion of the distal end 30 of the tool 24. The packaging body 22, 122, assumes the first configuration shown in FIG. 3. The packaging body 22, 122 remains in the packaging configuration. Secondary packaging 26 may be provided and adapted to receive the packaging body 22, 122. Example methods may include disposing the packaging body 22, 122 within the secondary packaging 26.

II. Packaging System Enabling Tool Rotation for Alignment

Figure 23:
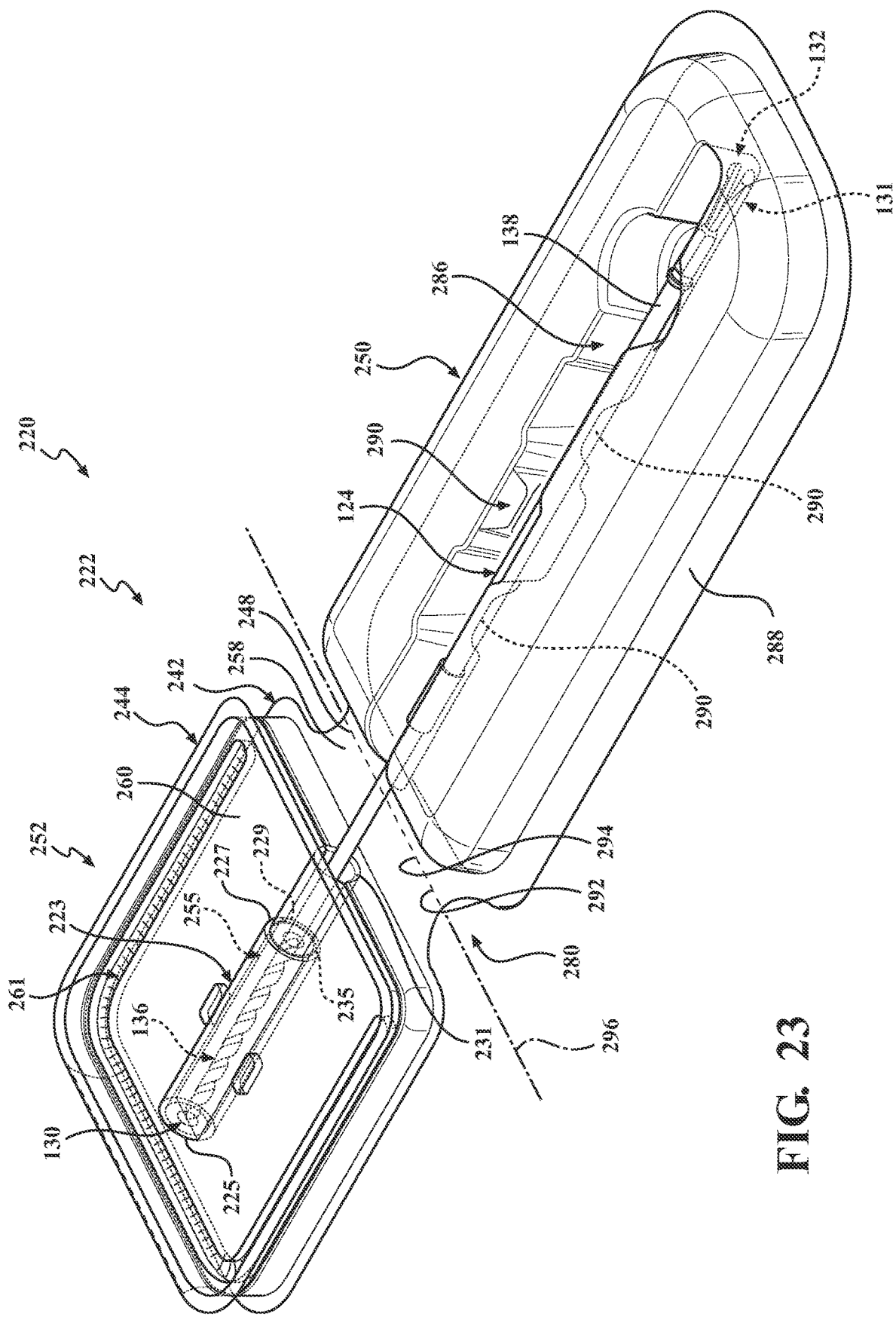
FIG. 23 is a perspective view of a packaging system in accordance with another example embodiment of the present disclosure with an elongate tool disposed within a packaging body.
Figure 25:
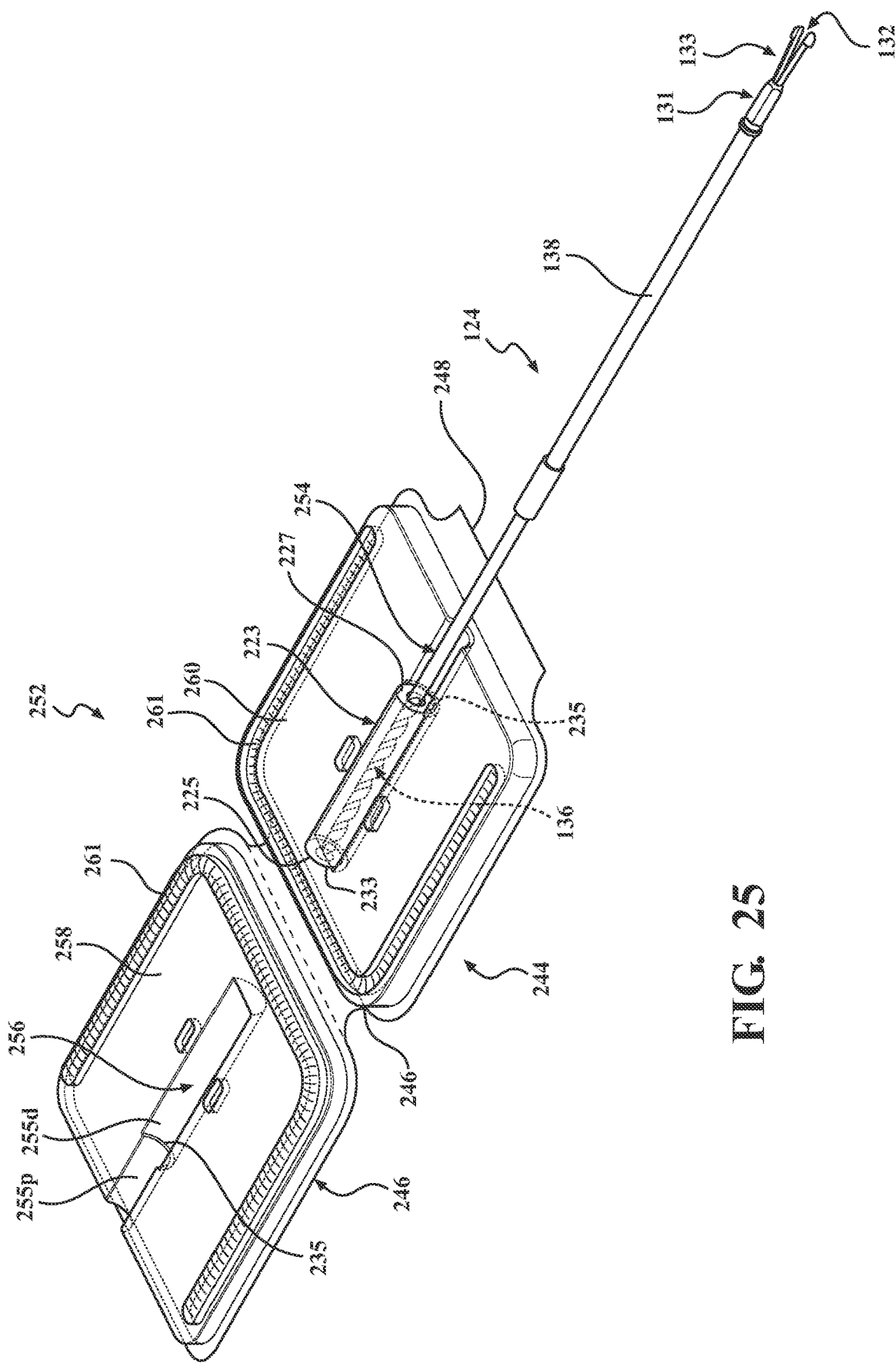
FIG. 25 is a perspective view of a casing of the packaging body of FIG. 23 in an opened or second configuration.

FIGS. 23 and 25 show a packaging system 220 including a packaging body 222 in accordance with another example, wherein the packaging body 222 is designed to mechanically facilitate installation of the tool 124, and in particular, where the tool 124 needs to rotate to install to the surgical device 28.

Like components of the packaging body 22, 122 of the previously described embodiments are identified with reference numerals increased by multiples of one hundred (100). Disclosure for the present example of the packaging body 222 abbreviated from the previously described embodiments is not to be construed as limiting unless specifically indicated. Any functionality and features related to the packaging body in the previous sections can be fully applied to the packaging body described in this section.

Figure 24:
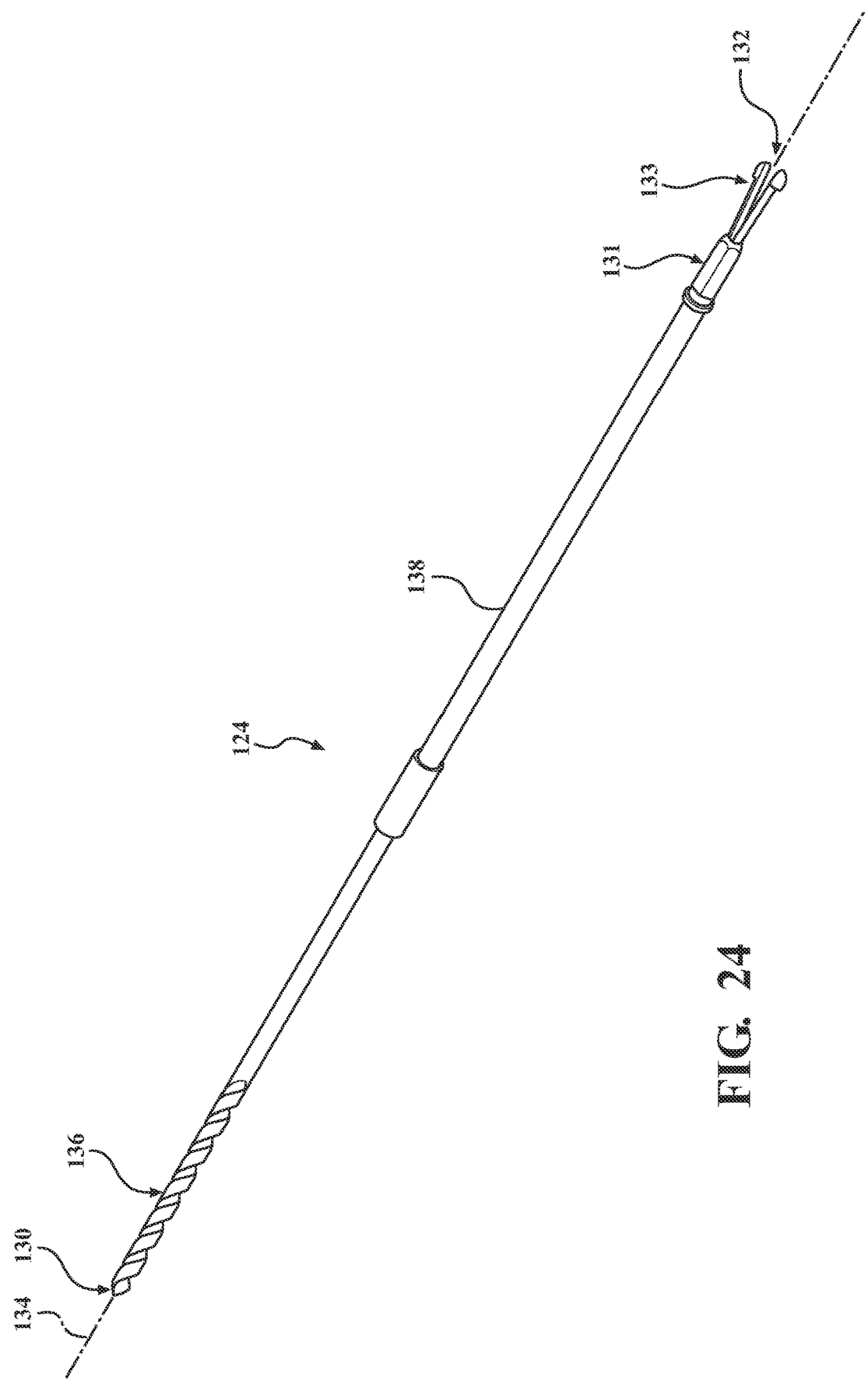
FIG. 24 is a perspective view of the elongate tool.

The packaging body 222 is configured to removably receive the tool 124 configured to be mounted on the surgical device 28. FIG. 24 shows another example tool 124 with like components relative to the previously described embodiment of the tool 124 identified with reference numerals increased by a multiple of one hundred (100). The tool 124 includes a distal end 130 and a proximal end 132 opposite the distal end 130. A length of the tool 124 is defined between the distal end 130 and the proximal end 132. A rotational axis 134 of the tool 124 may be defined between the distal end 130 and the proximal end 132. The length of the tool 124 is much greater than the width of the tool 124 such that the tool 124 may be defined as elongate. The tool 124 of FIG. 23 is circular in cross section and is configured to rotate about an axis of symmetry. The proximal end 132 is configured to be coupled to the surgical device 28, for example, the surgical robot R having the end effector EE (see FIG. 11). Alternatively, the surgical device 28 can be other mounted or hand-held surgical devices, such as those described above, or others not specifically described herein. FIG. 24 shows the tool 124 as a drill bit with a working portion 136 near or at the distal end 130, and a shaft or shank 138 extending to the distal end 130. The working portion 136 may include flutes extending proximally from the distal end 130.

The tool 124 may include alignment features 131 at or near the proximal end 132. With continued reference to FIG. 24, the alignment features 131 are coupled to the shank 138 and may be spaced part from the proximal end 132. As is described in greater detail below, the alignment features 131 are configured to facilitate rotationally locking the tool 124 to the surgical device 28 (or tool receiving portion of the surgical device) so that the surgical device 28 can rotate the tool 124 upon attachment. In order to axially lock the tool 124 to the surgical device 28, the tool 124 may include one or more resilient arms, generally indicated at 133. The resilient arms 133 may define the proximal end 132 of the tool 124. One suitable interface for facilitating the aforementioned rotational and axial locking is disclosed in commonly owned International Publication No. PCT/IB2018/056251, filed Aug. 17, 2018, the entire contents of which are hereby incorporated by reference. Secondary packaging 26 (see FIG. 1), such as the sealed pouch, the blister pack, or the like, may be provided and configured to receive the packaging body 222.

Returning to FIGS. 23 and 25, the packaging body 222 includes the casing 252. The casing 252 can be a permanently enclosed casing. In other words, the casing 252 would need to be partially or entirely destroyed or deformed in order to open the casing. Alternatively, the casing 252 can be configured to be freely opened and closed, as needed. In one example, the casing 252 can be configured as a clamshell casing, which may further include the first distal section 242 coupled to the second distal section 244 in a pivoting manner, such as any combination of the configurations described in the previous section. Alternatively, the casing 252 may include the removable couplers of the previously described embodiments of the packaging body 22, 122.

When the casing 252 is permanently enclosed, the casing 252 may comprise one integrally formed part, or may comprise several different parts. In one example, the first distal section 242 and the second distal section 244 may be joined together in a permanent manner. For example, the illustrated embodiment shows the primary surfaces 258, 260 of the first distal section 242 and the second distal section 244, respectively, joined through with high frequency welding. FIGS. 23 and 25 show a welding interface 261 on each of the primary surfaces 258, 260 and arranged in a generally U-shaped configuration. Overcoming the welding interface 261 may result in plastic deformation of one of the first and second distal sections 242, 244. Other suitable permanent joining means are contemplated, for example rivets or other fasteners, adhesives, etc.

The casing 252 is configured to receive the distal end 130 of the tool 124. The casing 252 may define the cavity 254, 256 disposed in at least one of the first and second distal sections 242, 244, respectively (collectively defined as cavity 255). With reference to FIG. 25, the cavity 254 may defined within the primary surface 258 of the first distal section 242, and the cavity 256 may defined within the primary surface 260 of the second distal section 244. The cavities 254, 256 of each of the first and second distal sections 142, 144 may be in alignment so as to receive the working portion 136 of the tool 124. Further, the cavity 255 may be substantially contoured to a distal region of the tool 124 such that a portion of the shank 138 is at least partially encased within the casing 252. FIG. 25 shows the cavities 254, 256 as being elongate.

The packaging body 222 may include the proximal section 250 coupled to the first distal section 242 at the proximal boundary 248. The proximal section 250 defines the cavity 286 sized to receive a proximal portion of the shank 138 of the tool 124 including the alignment features 131 and the resilient arms 133. The tool 124 may be secured within the cavity 286 with the one or more shaft couplers 290 which include, for example, the protrusions with the counter posing recesses to provide the interference fit to the shank 138 of the tool 124. The interference fit may be provided by a small amount of elastic deformation of the shaft coupler 290 that occurs as the tool 124 is urged within the cavity 286 of the proximal section 250.

In manners previously described, the proximal section 250 is configured to move between the packaging configuration and the installation configuration. The packaging configuration includes the proximal end 132 of the tool 124 disposed within the cavity 286 of the proximal section 250. The installation configuration includes pivoting the proximal section 250 relative to the casing 252, thereby exposing the proximal end 132 of the tool 124 outside the cavity 286 of the proximal section 250. The living hinge 292 and the cutouts 280 facilitate the relative pivoting between the casing 252 and the proximal section 250 at the proximal boundary 248. Moreover, the packaging body 222 may include the perforations 294 at the proximal boundary 248 configured to facilitate detachment of the casing 252 from the proximal section 250, or vice versa. The proximal section 250 may be detached from the casing 252 before or after mounting or installing the tool 124 on the surgical device 28. The distal end 130 of the tool 124, including the working portion 136, may remain safely packaged in the casing 252 subsequent to detachment of the proximal section 250 from the first distal section 242.

Of particular interest to the present embodiment is providing for self-aligned mounting of the tool 124 on the surgical device 28 without requiring undue manipulation or deformation of the casing 252. With continued reference to FIGS. 23 and 25, the packaging system 220 includes a sleeve 223 retained by the casing 252. The sleeve 223 is disposed within the cavity 255 of the casing 252. In particular, each of the cavities 254, 256 are positioned and shaped such that, with the first and second distal sections 242, 244 coupled to one another, at least a portion of the sleeve 223 is situated within the cavity 255. For reasons to be explained in greater detail, the cavity 255 is contoured to the sleeve 223, but sized to permit rotation of the sleeve 223 within the casing 252. In other words, with each of the cavities 254, 256 being semi-cylindrical, an inner diameter of the cavity 255 is greater than the outer diameter of the sleeve 223 to permit for rotation of the sleeve 223 relative to the casing 252. In alternative examples where the casing 252 is of one integrally formed part (without separate sections 242, 244), the cavity can be defined by the integrally formed part to capture the sleeve 223.

A combined force (e.g., static, frictional, compressive, etc.) that retains the sleeve 223 to the tool 124 is greater than a combined force that retains the sleeve 223 to the casing 242. For this reason, the tool 124 and sleeve 223 can freely rotate together relative to the casing 242 when the tool 124 is rotated relative to the casing 242. Meanwhile, for any rotational position of the tool 124, the sleeve 223 remains retained to the tool 124, until the casing 242 and the tool 124 are linearly separated along the axis of rotation.

The sleeve 223 may include a first end 225, a second end 227 opposite the first end 225, and a lumen 229 at least partially defined between the first and second ends 225, 227. FIGS. 23 and 25 show the lumen 229 extending from the first end 225 to the second end 227. In one example, the sleeve 223 and the lumen 229 are cylindrical. In another example, the sleeve 223 and/or lumen 229 may be spherical, semi-spherical, or any other shape that has an axis of symmetry for permitting rotation. The lumen 229 is sized to receive the working portion 136 of the tool 124, and more particularly sized to engage the working portion 136 of the tool 124 with an interference fit. In other words, with the sleeve 223 disposed within the cavity 254, 256 and the tool 124 engaging the sleeve 223, a rotation imparted to the shank 138 of the tool 124 causes the tool 124 and the sleeve 223 to rotate within the casing 252.

The casing 252 defines an opening 231 in communication with the cavity 255. The shank 138 of the tool 124 extends out of the opening 231 towards the proximal section 250, as shown in FIG. 23. The opening 231 may be formed between complementary ends of the cavities 254, 256 of the first and second distal sections 242, 244, respectively. With particular reference to FIG. 25, the cavity 255 may be elongate and further defined by a distal cavity portion 255d and a proximal cavity portion 255p. The distal cavity portion 255d extends between a closed cavity end 233 defined by the casing 252, and a stepped surface 235. The proximal cavity portion 255p extends between the stepped surface 235 and the opening 231. As best shown in FIG. 25, the stepped surface 235 is arranged such that a width of the proximal cavity portion 255p is narrower than a width of the distal cavity portion 255d. The sleeve 223 is disposed within the distal cavity portion 255d. In other words, the first end 225 of the sleeve 223 is positioned adjacent the closed cavity end 233 of the cavity 255, and the second end 227 of the sleeve 223 is positioned adjacent the stepped surface 235. With the outer diameter of the sleeve 223 greater than the width of the proximal cavity portion 255p, the sleeve 223 is retained within the casing 252. More specifically, the sleeve 223 is prevented from being removed from the casing 252 through the proximal cavity portion 255p and the opening 231, particularly during removal of the tool 124 from the sleeve 223 in a manner to be described. The arrangement may result in the sleeve 223 being substantially encased within the casing 252. As opposed to the stepped surface 235, a taper or other barrier may be provided to facilitate retention of the sleeve 223 within the casing 252. While the sleeve 223 is retained within the casing 252, the outer diameter of the tool 124 is less than the width of the proximal cavity portion 255p such that the tool 124 is removable from the casing 252 through the opening 231.

This casing configuration provides continuous protection from the working portion 136 of the tool 124 simultaneously while enabling the tool 124 to be retained and rotatable within the casing 252 during installation. Furthermore, when the casing 252 is permanently closed, the working portion 136 can be withdrawn from the casing 252 and reinserted into the casing 252 as needed through the opening 231, without requiring re-assembly or causing destruction of the casing 252.

As mentioned, the working portion 136 of the tool 124 engages the sleeve 223 with an interference fit. The length of the sleeve 223 and the lumen 229 may be sized to receive an entirety of the flutes of the working portion 136 of the drill bit of FIG. 24. At the same time, however, the interference fit is capable of being overcome with sufficient force applied to the casing 252 relative to the tool 124, or vice versa, without the flutes removing material from the lumen 229 of the sleeve 223 (e.g., galling). In certain embodiments, the packaging body 222 is formed from a first material, and the sleeve 223 is formed form a second material different than the first material. The first and second materials may be plastics or other suitable polymer, metal, composite, and the like, with the second material forming the sleeve 223 being sufficiently more robust to prevent the galling during removal of the working portion 136 from the sleeve 223. A kit may be provided including the packaging body 222, the sleeve 223, and the tool 124.

Figure 26:
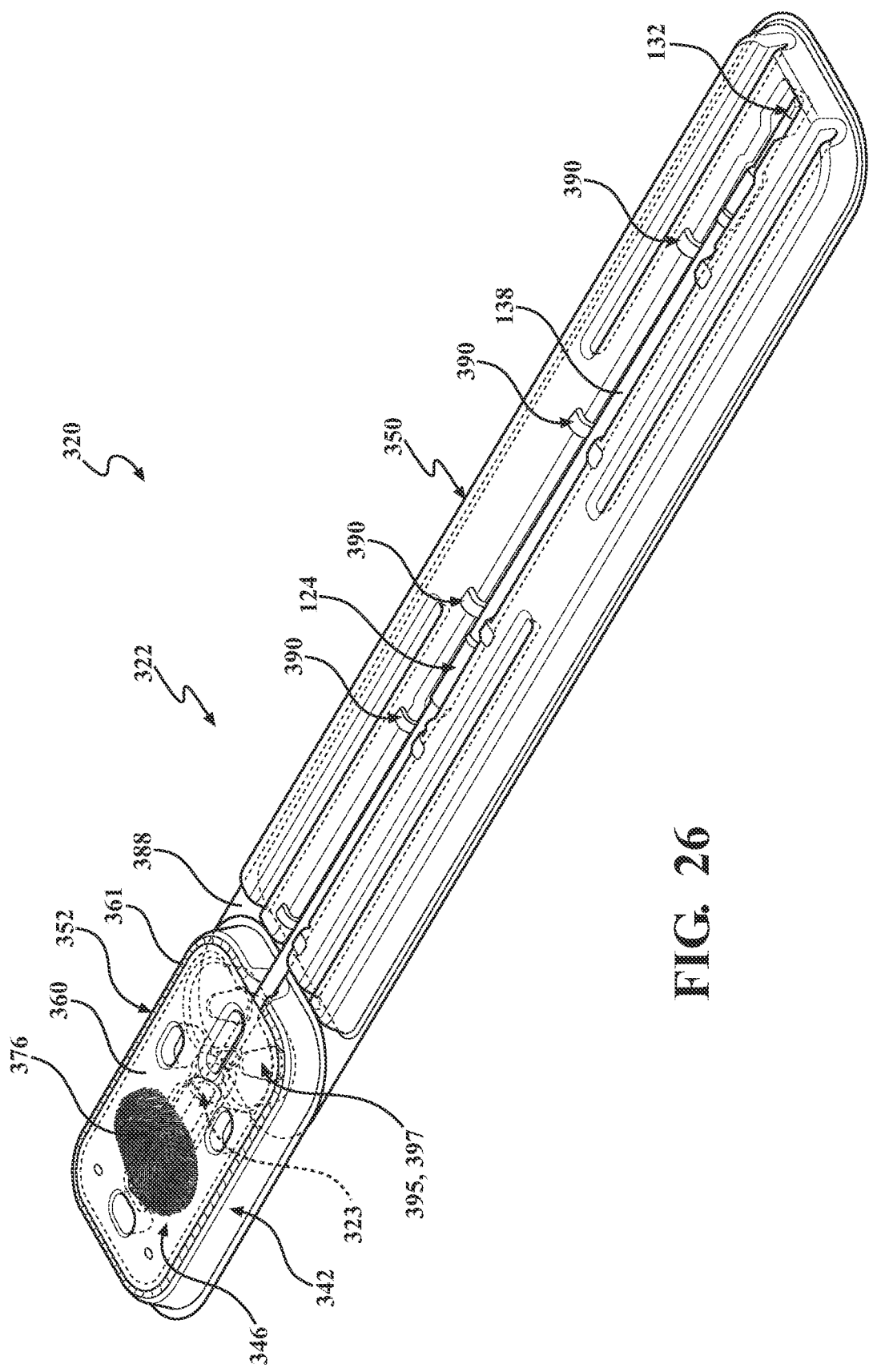
FIG. 26 is a perspective view of a packaging system in accordance with another example embodiment of the present disclosure with an elongate tool disposed within the packaging body.
Figure 27:
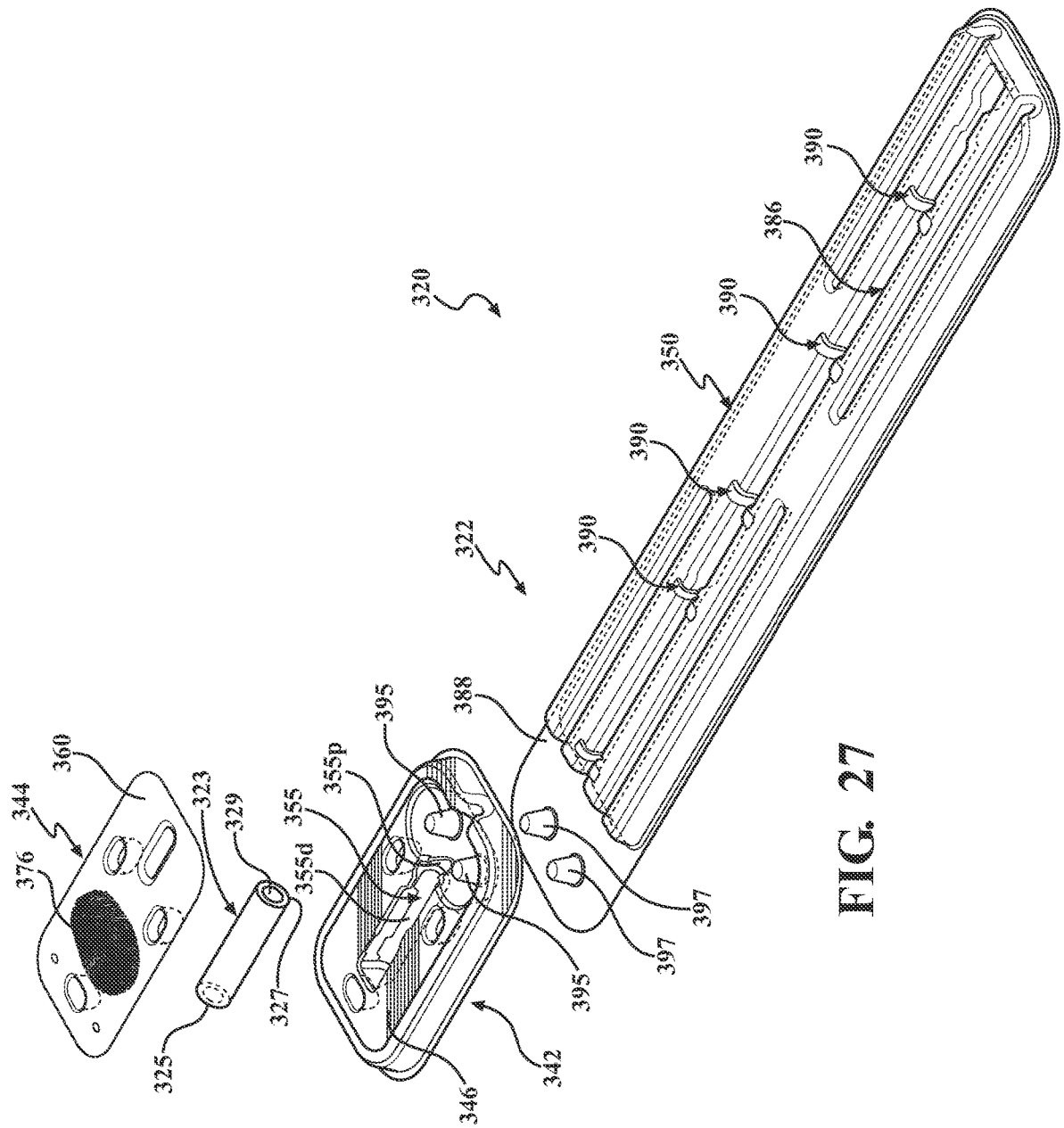
FIG. 27 is an exploded view of the packaging system of FIG. 26.
Figure 28:
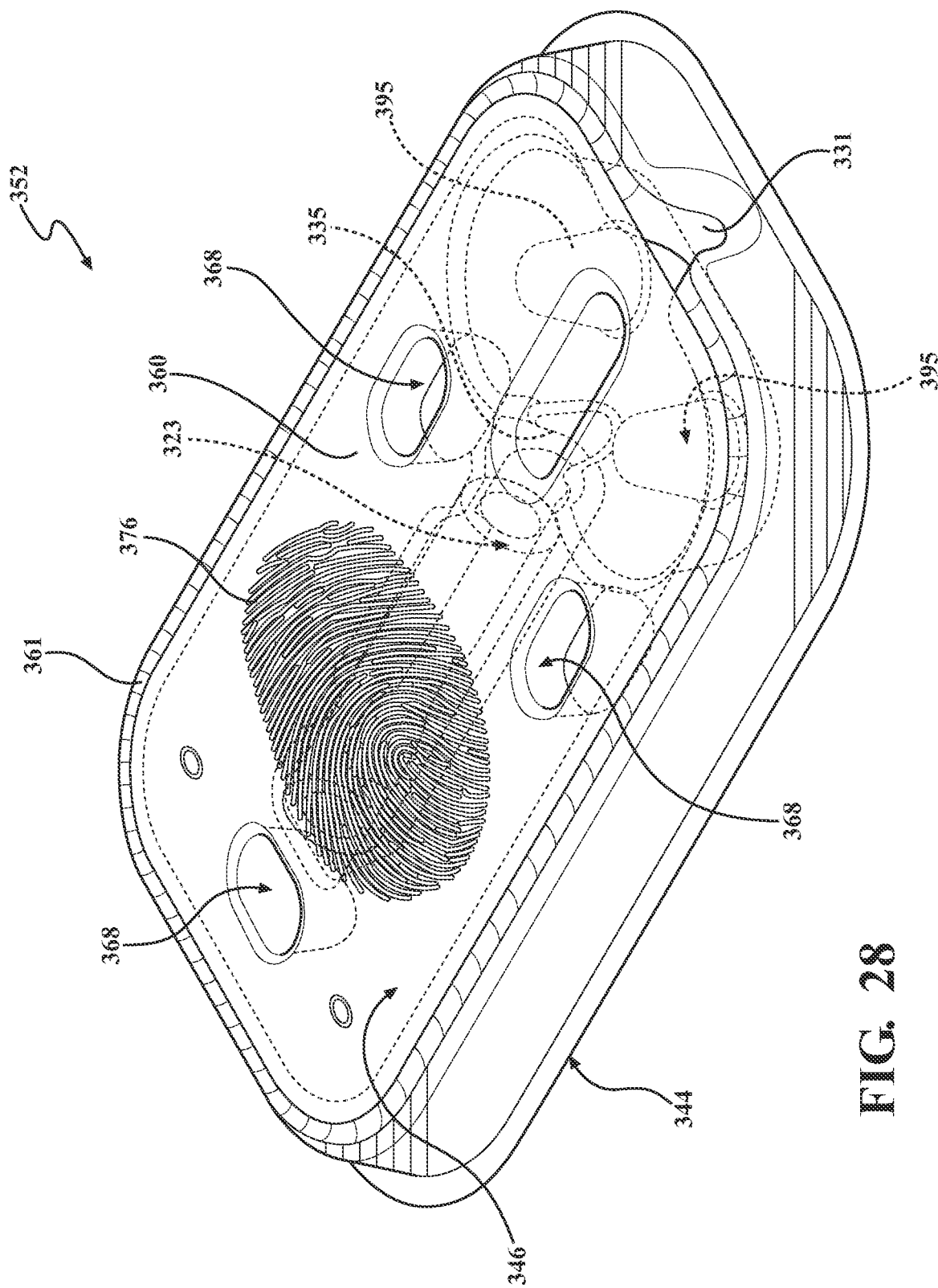
FIG. 28 is a perspective view of a casing of the packaging body of FIG. 26

FIGS. 26-28 show a packaging system 320 including a packaging body 322 in accordance with another example, wherein the packaging body 322 is designed to mechanically facilitate installation of the tool 124 including the alignment features 131 for rotationally locking the tool 124 to the surgical device 28 (or tool receiving portion of the surgical device) so that the surgical device 28 can rotate the tool 124 upon attachment. Like components of the packaging body 22, 122, 222 of the previously described embodiment(s) are identified with reference numerals increased by multiples of one hundred (100). Disclosure for the present example of the packaging body 322 abbreviated from the previously described embodiments is not to be construed as limiting unless specifically indicated. Any functionality and features related to the packaging body in the previous sections can be fully applied to the packaging body described in this section.

FIGS. 26 and 27 show the packaging body 322 including the casing 352. The casing 352 can be a permanently enclosed casing. In other words, the casing 352 would need to be partially or entirely destroyed or deformed in order to open the casing. When the casing 352 is permanently enclosed, the casing 352 may comprise one integrally formed part, or may comprise several different parts. In one example, the first distal section 342 and the second distal section 344 may be joined together in a permanent manner. For example, the illustrated embodiment shows the primary surfaces 358, 360 of the first distal section 342 and the second distal section 344, respectively, joined through with high frequency welding. FIGS. 26 and 28 show the welding interface 361 on each of the primary surfaces 358, 360 and arranged in a generally U-shaped configuration. Overcoming the welding interface 361 may result in plastic deformation of one of the first and second distal sections 342, 344. Other suitable permanent joining means are contemplated, for example rivets or other fasteners, adhesives, etc. Alternatively, the casing 352 can be configured to be freely opened and closed, as needed. In one example, the casing 352 can be configured as a clamshell casing, which may further include the first distal section 342 coupled to the second distal section 344 in a pivoting manner, such as any combination of the configurations described in the previous section.

The packaging body 322 may include the couplers 368 for facilitating assembly of the first and second distal sections 342, 344. The couplers 368 may cooperate to align the second distal section 344 with the first distal section 342 prior to being joined through with high frequency welding. Alternatively, the couplers 368 may operate by interference or friction fit to facilitate the casing 352 being freely opened and closed, as needed.

The casing 352 is configured to receive the distal end 130 of the tool 124. The casing 352 may define the cavity 355 within at least one of the first and second distal sections 342, 344. With reference to FIG. 27, the cavity 355 may defined within the primary surface 358 of the first distal section 342, and may be substantially contoured to a distal region of the tool 124 such that a portion of the shank 138 is at least partially encased within the casing 352.

The proximal section 350 defines the cavity 386 sized to receive a proximal portion of the shank 138 of the tool 124 including the alignment features 131 and the resilient arms 133. The tool 124 may be secured within the cavity 386 with the one or more shaft couplers 390 which include, for example, the protrusions with the counter posing recesses to provide the interference fit to the shank 138 of the tool 124. The interference fit may be provided by a small amount of elastic deformation of the shaft coupler 390 that occurs as the tool 124 is urged within the cavity 386 of the proximal section 350.

The proximal section 350 may be removably coupled to the casing 352, and in particular to the first distal section 342. FIG. 27 shows the proximal section 350 including a pair of lugs 397 extending from the primary surface 388 of the proximal section 350, and a pair of cavities 395 within the casing 352. The cavities 395 are sized to snugly and removably receive the lugs 397. The cavities and lugs 395, 397 are complementarily positioned such that, when the lugs 397 are disposed within the cavities 395, the sleeve 322 is aligned with the cavity 386 of the proximal section 350 in the arrangement shown in FIG. 26. The alignment facilitates the distal region of the tool 124 being disposed within the sleeve 323, and a proximal region of the tool 124 being disposed within the cavity 386 of the proximal section 350.

The cavities and lugs 395, 397 may or may provide interference engagement to maintain coupling of the casing 352 and the proximal section 350 until the user affirmatively manipulates the packaging body 322 to overcome the interference engagement. In one example, cavities and lugs 395, 397 do not provide a meaningful friction fit, but rather the tool 124 cooperates with the packaging body 322 to maintain coupling of the casing 352 and the proximal section 350. As mentioned, the distal end 130 of the tool 124 is disposed within the casing 352, and the proximal portion of the shank 138 of the tool 124 is disposed within the proximal section 350. More particularly, the sleeve 323 provides an interference fit with the distal end 130 of the tool 124, and the shaft couplers 390 provide an interference fit with the shank 138 of the tool 124. Thus, the tool 124 itself may effectively provide the structure "bridges" the casing 352 and the proximal section 350 to couple the same, with the cavities and lugs 395, 397 preventing any relative movement. For example, the cavities and lugs 395, 397 may prevent inadvertent movement of the proximal section 350 relative to the casing 352 along the tool axis 134 (see FIG. 24), and the cavities and lugs 395, 397 along with the primary surface 388 of the proximal section 350 may prevent inadvertent rotation the proximal section 350 relative to the casing 352 about the tool axis 134.

The proximal section 350 is removably coupled to the casing 352. To decouple the proximal section 350 from the casing 352, for example, prior to mounting or installing the tool 124 on the surgical device 28, the user may provide an input to the packaging body 322 to simultaneously or sequentially overcome the interference engagement provided by the shaft couplers 390, and further remove the lugs 397 from within the cavities 395. For example, the user may support the casing 352 with one hand and provide a downward force to the proximal section 350 near the distal end 132 of the tool 124. The force may the shaft couplers 390 to sequentially disengage in the distal direction (the proximal section 350 may flex to facilitate the disengagement), and once the shaft couplers 390 are disengaged, the lugs 397 may be removed from within the cavities 395 with relative ease. The distal end 130 of the tool 124, including the working portion 136, may remain safely packaged in the casing 352 subsequent to detachment of the proximal section 350 from the first distal section 342.

With continued reference to FIGS. 26-28, the packaging system 320 includes the sleeve 323 retained by the casing 352. The sleeve 323 is disposed within the cavity 355 of the casing 352. In particular, with the first and second distal sections 342, 344 coupled to one another, either permanently or removably, at least a portion of the sleeve 323 is situated within the cavity 355. For reasons to be explained in greater detail, the cavity 355 is contoured to the sleeve 323, but sized to permit rotation of the sleeve 323 within the casing 352. In other words, the cavity 355 may be at least substantially cylindrical, an inner diameter of the cavity 355 is greater than the outer diameter of the sleeve 323 to permit for rotation of the sleeve 323 relative to the casing 352. In alternative examples where the casing 352 is of one integrally formed part (without separate sections 342, 344), the cavity can be defined by the integrally formed part to capture the sleeve 323.

A combined force (e.g., static, frictional, compressive, etc.) that retains the sleeve 323 to the tool 124 is greater than a combined force that retains the sleeve 323 to the casing 342. For this reason, the tool 124 and sleeve 323 can freely rotate together relative to the casing 342 when the tool 124 is rotated relative to the casing 342. Meanwhile, for any rotational position of the tool 124, the sleeve 323 remains retained to the tool 124, until the casing 342 and the tool 124 are linearly separated along the axis of rotation.

The sleeve 323 may include a first end 325, a second end 327 opposite the first end 325, and a lumen 329 at least partially defined between the first and second ends 325, 327. FIGS. 27 and 28 show the lumen 329 extending from the first end 325 to the second end 327. In one example, the sleeve 323 and the lumen 329 are cylindrical. In another example, the sleeve 323 and/or lumen 329 may be spherical, semi-spherical, or any other shape that has an axis of symmetry for permitting rotation. The lumen 329 is sized to receive the working portion 136 of the tool 124, and more particularly sized to engage the working portion 136 of the tool 124 with an interference fit. In other words, with the sleeve 323 disposed within the cavity 355 and the tool 124 engaging the sleeve 323, a rotation imparted to the shank 138 of the tool 124 causes the tool 124 and the sleeve 323 to rotate within the casing 352.

The casing 352 defines an opening 331 in communication with the cavity 355. The shank 138 of the tool 124 is configured to extend out of the opening 331 towards the proximal section 350. The opening 331 may be formed between the first and second distal sections 342, 344, respectively. With particular reference to FIG. 25, the cavity 355 may be elongate and further defined by a distal cavity portion 355*d* and a proximal cavity portion 355*p*. The distal cavity portion 355*d* extends between a closed cavity end 233 defined by the casing 352, and a stepped surface 335. The proximal cavity portion 355*p* extends between the stepped surface 335 and the opening 331. As best shown in FIG. 28, the stepped surface 335 is arranged such that a width of the proximal cavity portion 355*p* is narrower than a width of the distal cavity portion 355*d*. The sleeve 323 is disposed within the distal cavity portion 355*d*. In other words, the first end 325 of the sleeve 323 is positioned adjacent the closed cavity end 333 of the cavity 355, and the second end 327 of the sleeve 323 is positioned adjacent the stepped surface 335. With the outer diameter of the sleeve 323 greater than the width of the proximal cavity portion 355*p*, the sleeve 323 is retained within the casing 352. More specifically, the sleeve 323 is prevented from being removed from the casing 352 through the proximal cavity portion 355*p* and the opening 331, particularly during removal of the tool 124 from the sleeve 323. The arrangement may result in the sleeve 323 being substantially encased within the casing 352. As opposed to the stepped surface 335, a taper or other barrier may be provided to facilitate retention of the sleeve 323 within the casing 352. While the sleeve 323 is retained within the casing 352, the outer diameter of the tool 124 is less than the width of the proximal cavity portion 355p such that the tool 124 is removable from the casing 352 through the opening 331.

This casing configuration provides continuous protection from the working portion 136 of the tool 124 simultaneously while enabling the tool 124 to be retained and rotatable within the casing 352 during installation. Furthermore, when the casing 352 is permanently closed, the working portion 136 can be withdrawn from the casing 352 and reinserted into the casing 352 as needed through the opening 331 without requiring re-assembly or causing destruction of the casing 352.

As mentioned, the working portion 136 of the tool 124 engages the sleeve 323 with an interference fit. The length of the sleeve 323 and the lumen 329 may be sized to receive an entirety of the flutes of the working portion 136 of the drill bit of FIG. 26. At the same time, however, the interference fit is capable of being overcome with sufficient force applied to the casing 352 relative to the tool 124, or vice versa, without the flutes removing material from the lumen 329 of the sleeve 323 (e.g., galling). In certain embodiments, the packaging body 322 is formed from a first material, and the sleeve 323 is formed form a second material different than the first material. The first and second materials may be plastics or other suitable polymer, metal, composite, and the like, with the second material forming the sleeve 323 being sufficiently more robust to prevent the galling during removal of the working portion 136 from the sleeve 323. A kit may be provided including the packaging body 322, the sleeve 323, and the tool 124.

Figure 30:
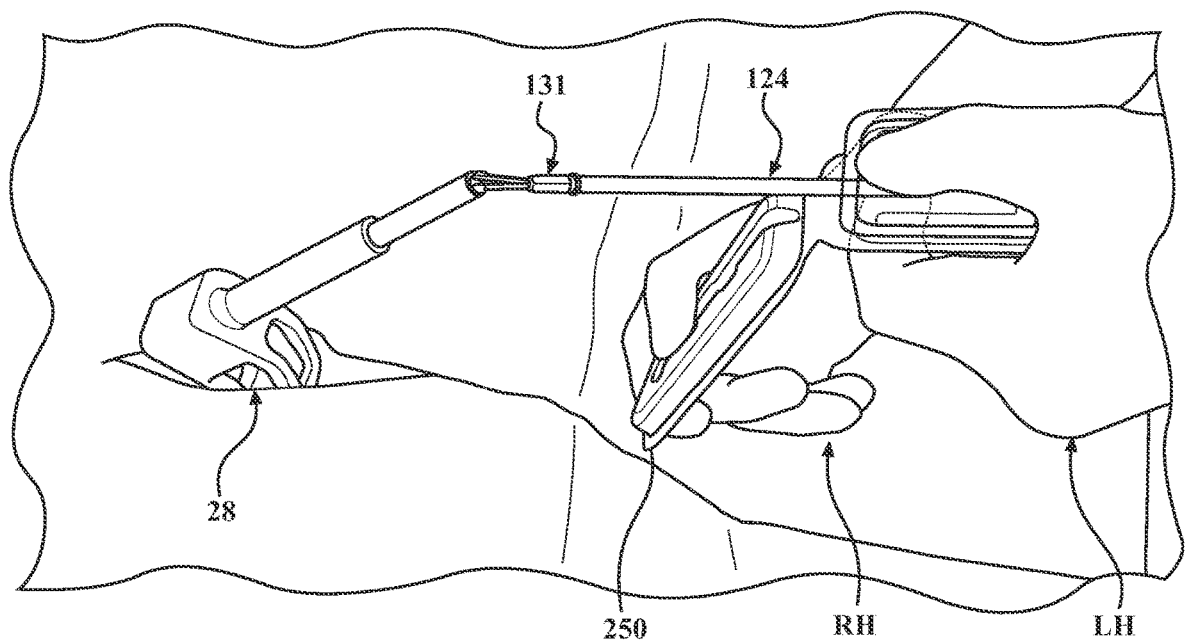
FIG. 30 shows a step of an example method of mounting the elongate tool of FIG. 24 on the surgical device with the packaging body of FIG. 23.

Example methods of mounting the elongate tool 124 on the surgical device 28 with the packaging system 220, 320 are described with reference to FIGS. 30-33. The tool 124 is disposed within the packaging body 222, 322, and the packaging body 222, 322 including the tool 124 is initially positioned away from the surgical device 28, in this example the end effector. Again, the surgical device 28 can be a hand-held device instead of an end effector. FIG. 30 shows the packaging body 222 being moved from the packaging configuration with the proximal end 132 of the tool 124 disposed within the cavity 286 to the installation configuration. The user grasps the packaging body 222 with, for example, the right hand RH and the left hand LH as shown in FIG. 30. While holding the packaging body 222, the proximal section 250 is articulated or bent about the proximal boundary 248 relative to the casing 252 to remove or expose the proximal end 132 of the tool 124 from the cavity 286 of the proximal section 250. The relative articulation exposes the orientation features 131 of the tool 124.

Figure 31:
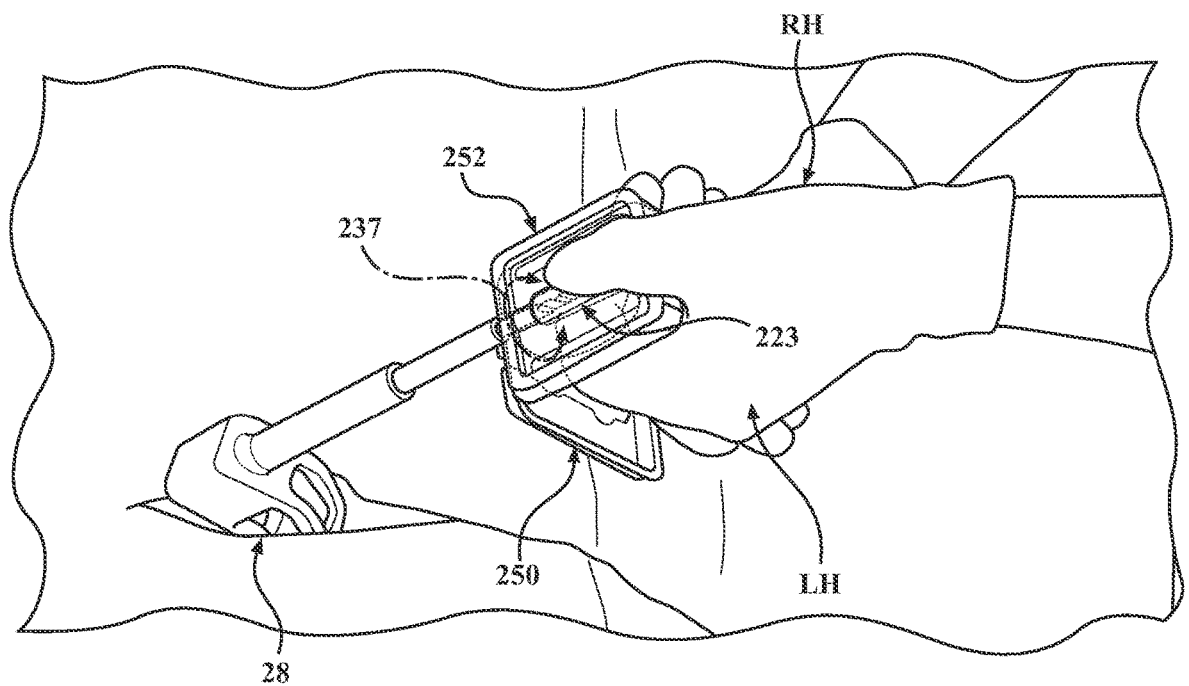
FIG. 31 shows another step of the example method of mounting the elongate tool on the surgical device.

The proximal end 132 of the tool 124 is mounted on the surgical device 28 while the distal end 130 of the tool 124 remains disposed within the sleeve 223 retained within the casing 252. FIGS. 30 and 31 show the user slidably moving the tool 124 into a desired engagement with the surgical device 28 while supporting the casing 252. In this example, the user is supporting the casing 252 with the left hand LH and the proximal section 250 with the right hand RH as the shank 138 of the tool 124 is slidably received by the surgical device 28.

As the proximal end 132 is directed into the surgical device 28, the working portion 136 of the tool 124 remains within the sleeve 223. The alignment features 131 engage complementary alignment features (not shown) associated with the surgical device 28. The initial engagement of the complementary alignment features 131 are configured to impart rotation to the tool 124 to provide for further advancement of the tool 124 within the surgical device 28, as detailed in commonly owned International Publication No. PCT/IB2018/056251, filed Aug. 17, 2018, the entire contents of which are hereby incorporated by reference. The rotation of the tool 124 imparts like rotation to the sleeve 223 within the casing 252 owing to the interference fit between the working portion 136 and the lumen 229 of the sleeve 223 (represented as arrow 237 in FIG. 31). In other words, the self-aligning causes rotation of the tool 124 and the sleeve 223 relative to the casing 252. The advantages of the packaging system 220 are readily realized as providing for self-aligned mounting of the tool 124 on the surgical device 28 without requiring manual rotation or further manipulation of the shank 138 of the tool 124 and/or the casing 252 being grasped by the user. After mounting the tool 124 on the surgical device 28, the method may further include the step of detaching the proximal section 250 from the casing 252 at the proximal boundary 248. The proximal boundary 248 includes the perforations 294 to facilitate detaching the proximal section 250.

Figure 32:
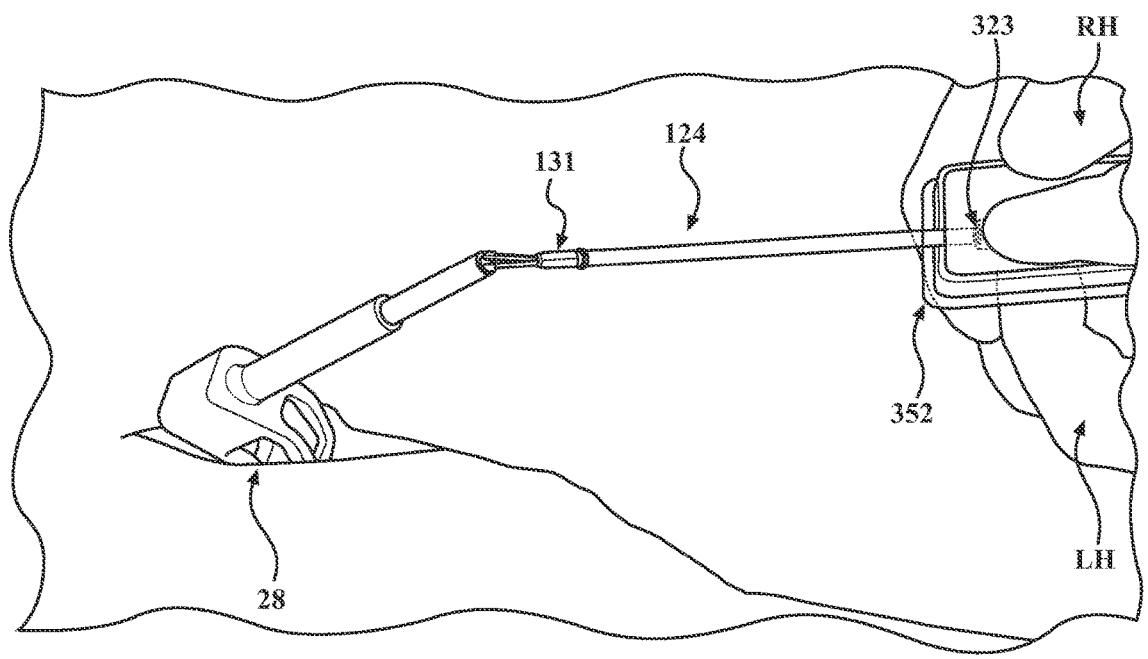
FIG. 32 a step of an example method of mounting the elongate tool of FIG. 24 on the surgical device with the packaging body of FIG. 26.
Figure 33:
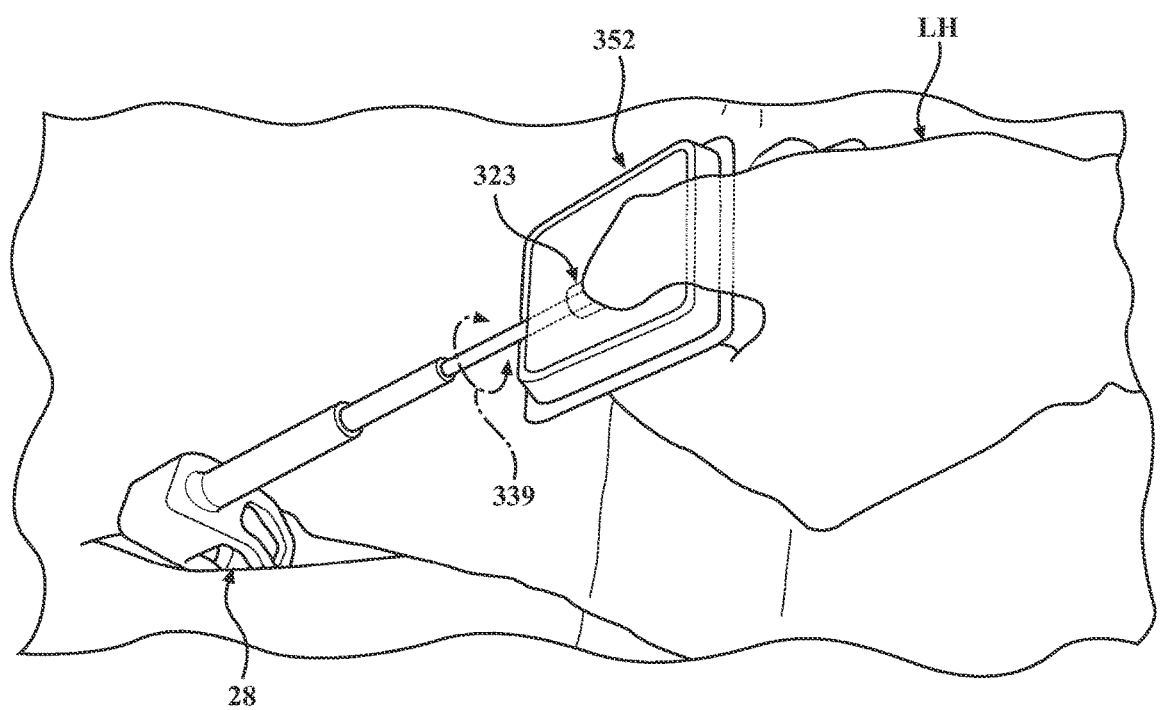
FIG. 33 shows another step of the example method of mounting the elongate tool on the surgical device.

In another example method shown in FIGS. 32 and 33, the proximal section 350 may be decoupled from the casing 352 prior to mounting or installing the tool 124 on the surgical device 28 in manners previously described. With one or both of the right hand RH and the left hand LH, the user mounts the proximal end 132 of the tool 124 on the surgical device 28. FIG. 32 shows the user supporting the casing 352 with both the right hand RH and the left LH, and the user may remove one of the hands RH, LH after a portion of the shank 138 of the tool 124 is confidently within the surgical device 28 such that suitable engagement is ensured. Again, as the proximal end 132 is directed into the surgical device 28, the alignment features 131 engage complementary alignment features the tool 124 and the sleeve 332 rotate within the casing 352 (represented as arrow 339 in FIG. 33).

The user may wish to delay between the step of mounting the tool 124 on the surgical device 28 and/or removing the packaging body 222, 322 to expose the distal end 130 of the tool 124. The working portion 136 of the tool 124 remains secured and protected within the casing 252, 352 after the tool 124 is mounted on the surgical device 28. Should inadvertent contact occur with the tool 124, the risk of contamination and/or injury to the user and/or surgical device 28 is greatly reduced. Once desired, the casing 252, 352 (and the sleeve 223, 323) may be removed from the tool 124 to expose the working portion 136 of the tool 124. The user may apply an input to the casing 252, 352 to apply a force parallel to the axis 134 of the tool 124 (see FIGS. 24 and 26). The interference engagement between the tool 124 and the sleeve 223, 323 is overcome, and the sleeve 223, 323 is slidably removed from the working portion 136. Owing to the aforementioned stepped surface 235, 335 providing the proximal cavity portion 255p, 355p that is narrower than the outer diameter of the sleeve 223, 323, the sleeve 223, 323 remains disposed within the cavity 255, 355 subsequent to removal of the tool 124. The working portion 136 of the tool 124 is now exposed and ready for use during a surgical procedure. It is to be appreciated that the user has not touched the tool 124 in any significant manner, and the working portion 136 of the tool 124 was shielded from contamination and to avoid injury. The above-described methods can be utilized with any configuration of the packaging system that includes the sleeve 223, 323.

III. Indicia for Intuitive Operation of the Packaging System

Figure 29:
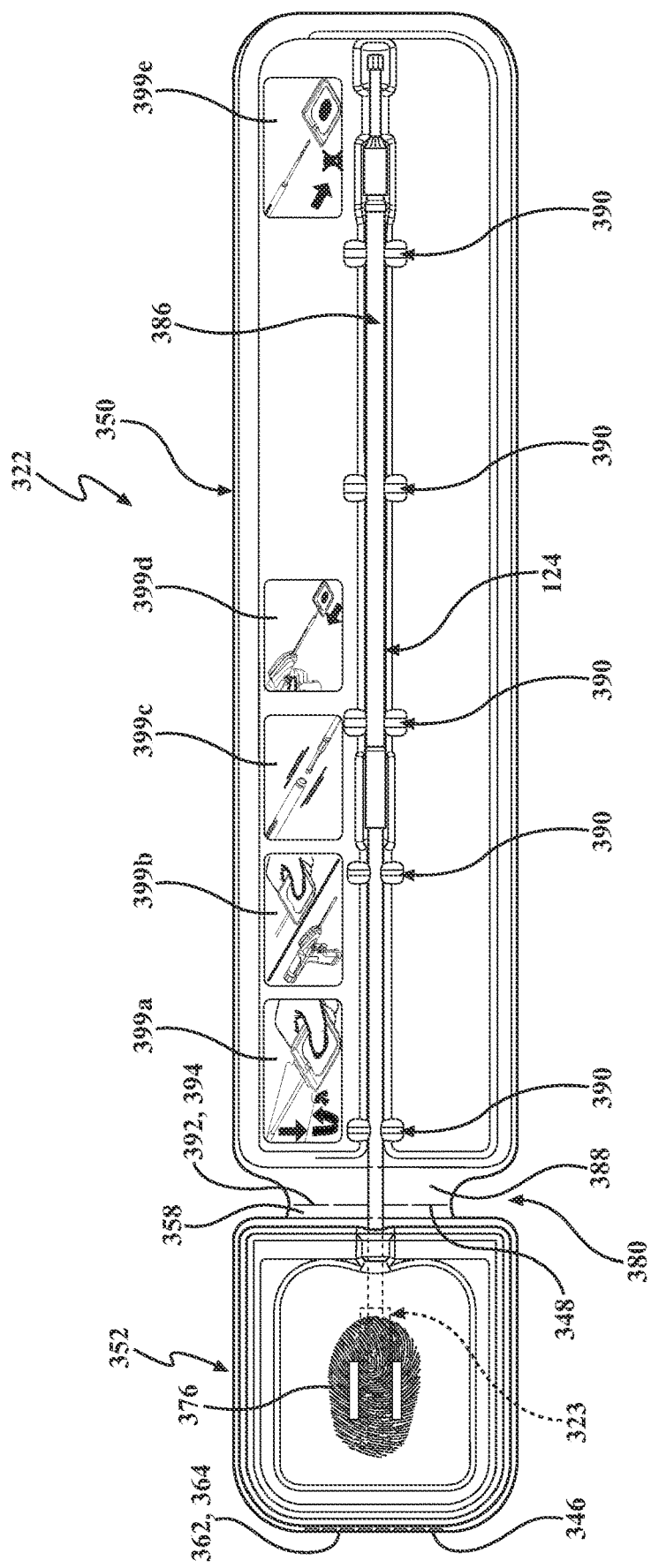
FIG. 29 is a top plan view of a packaging system in accordance with another example embodiment of the present disclosure with instructional markings disposed on a proximal section of the packaging body.

With continued reference to FIGS. 26-28 ad further reference to FIG. 29, the packaging body 322 may include a finger grip 376 configured to be grasped by at least one finger of the user during manipulation of the packaging body 322. Moreover, the finger grip 376 may be positioned, sized, and/or shaped in a manner to provide an indication to the user of a proper manner to hold the packaging body 322 during insertion of the tool 124 on the surgical device 28. The finger grip 376 shown in FIGS. 26-29 is a texturized feature representative of a thumb print of a human hand. Further, the finger grip 376 is disposed on the primary surface 360 of the second distal section 344 of the casing 352, which may be considered the uppermost surface of the packaging body 322. Owing to the overall geometry of the packaging body 322, including the cavity 386 of the proximal section 350 opening upwardly, the user may be inclined to hold the primary surface 360 of the second distal section 344 upward, which assumes a natural position for the thumb (with one or more fingers supporting an underside of the casing 352 opposite the primary surface 360). Thus, the texturized feature representative of the thumb print provides an indication for the user to position their thumb on the finger grip 376 during insertion of the tool 124 on the surgical device 28. Similarly, the texturized feature representative of the thumb print is generally oriented perpendicular to the tool axis 124, which, again, may be the most natural for the thumb with the packaging body 322 being advanced towards the surgical device 28 in along the tool axis 124. It is appreciated that the texturized feature representative of the thumb print may be included on any of the implementations of the packaging body 22, 122, 222.

In certain implementations, at least a portion of the casing 352 may be colored differently than the proximal section 350. As best shown in FIGS. 27 and 28, the first distal section 342 is colored (represented by horizontal hatchings indicative of the color blue), for example, formed from a colored thermoformed plastic. The second distal section 344 and/or the proximal section 350 may be at least substantially translucent, for example, clear. The coloring of the casing 352 may provide several advantages. First, the coloring may provide a visual indication of a location of the working portion 136 of the tool 124. Second, the coloring may provide an impression to the user that the casing 352 is the primary functional component of the tool 124. In other words, the proximal section 350 being clear may indicate that the proximal section 350 is to be decoupled and discarded while the casing is to remain removably retained on the working portion 136 of the tool 124 for mounting the tool 124 on the surgical device 28. The coloring may also direct the user's attention to the texturized feature representative of the thumb print, which in combination with the coloring itself, may provide the user with an indication of the manner by which to hold or manipulate the packaging body 322 to mount the tool 124 on the surgical device 28. Third, the coloring may provide contrast with the background environment once the tool 124 is mounted on the surgical device 28. As previously described in detail, the working portion 136 of the tool 124 may remain secured and protected within the casing 352 after the tool 24 is mounted on the surgical device 28. Should inadvertent contact occur with the tool 124, the risk of contamination and/or injury to the user and/or surgical device 28 is greatly reduced. Should the casing 352 be clear, for example, the tool 124 (and casing 352) may be less noticeable to those moving about the surgical suite. The contrast provided by the coloring to the casing 352 may limit or prevent the inadvertent contact. It is appreciated that the coloring feature may be included on any of the implementations of the packaging body 22, 122, 222.

With particular reference to FIG. 29, a series of instructional markings 399 may be disposed on the packaging body 322. The instructional markings 399 may provide visual indication of steps for mounting the tool 124 on the surgical device 28. The instructional markings 399 may be, for example, illustrations, pictures, or the like. FIG. 29 shows the instructional markings disposed on the proximal section 350 and including five instructional markings 399*a-e* each representative of a step of mounting the tool 124 on the surgical device 28. A first of the instructional markings 399*a* shows the user how to move the packaging body 322 from the packaging configuration to the installation configuration, in particular, by articulating or bending the proximal section 350 about the proximal boundary 348 relative to the casing 352 to remove or expose the proximal end 132 of the tool 124. Additionally or alternatively, first of the instructional markings 399*a* shows how to decoupling and/or detaching the proximal section 350 from the casing 352.

A second of the instructional markings 399*b* shows the user how to support the casing 352. It is appreciated that the finger grip 376 (i.e., the texturized feature representative of the thumb print) is shown in the second instructional marking 399*b* to assist the user with identifying the proper manner to grasp and orient the casing 352 and the tool 124, respectively.

A third and fourth of the instructional markings 399*c*, 399*d* shows the user how to mount the proximal end 132 of the tool 124 on the surgical device 28. An arrow shown on the fourth instructional markings 399*d* indicates the shank 138 of the tool 124 is moved axially towards the surgical device 28 (shown supported by one of the user's hands) to ensure suitable engagement.

A fifth of the instructional markings 399*e* shows the user how to expose the working portion 136 of the tool 124. An arrow is indicative of the force to be applied to the casing 352 to overcome the interference engagement between the tool 124 and the sleeve 323 to slidably remove the working portion 136. The working portion 136 of the tool 124 is now exposed and ready for use during a surgical procedure. It is appreciated that the instructional markings 399 may be included on any of the implementations of the packaging body 22, 122, 222.

From FIG. 29, it should also be appreciated that features from the embodiments of the packaging body 22, 122, 222, 322 may be combined without limitation. FIG. 29 shows certain features from the embodiment of FIGS. 26-28 (e.g., the geometry of the proximal section 350 including the shaft couplers 390, geometry of the casing 352, and the finger grip 376), and certain features from the embodiment of FIGS. 23 and 25 (e.g., the living hinge 362 including the perforations 264, and the living hinge 392 including the perforations 394), and certain features from the embodiment of FIGS. 3-10 (e.g., the casing 352 being the clamshell casing). The embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A packaging system for a tool that has a working portion and a shaft, the packaging system comprising:
   a casing comprising a distal section defining a cavity configured to receive the working portion of the tool; and
   a proximal section coupled to the distal section and being configured to receive the shaft of the tool, and the proximal section being configured to detach from the distal section; and
   wherein at least a portion of the distal section comprises a colored indicator to provide a visual indication of a location of the working portion of the tool.

2. The packaging system of claim 1, wherein the colored indicator is colored differently than the proximal section.

3. The packaging system of claim 1, wherein the at least a portion of the distal section that comprises the colored indicator is formed of colored thermoformed plastic.

4. The packaging system of claim 1, wherein the distal section and the proximal section are translucent.

5. The packaging system of claim 1, wherein the distal section comprises:
   a first distal section comprising a first boundary and a second boundary;
   a second distal section coupled to the first distal section at the first boundary;
   the first and second distal sections being configured to collectively define the cavity that receives the working portion; and
   the first and second distal sections being configured to detachably couple to one another.

6. The packaging system claim 5, wherein the second distal section is pivotable relative to the first distal section at the first boundary such that the first distal section and the second distal section collectively provide a clamshell casing to the working portion of the tool.

7. The packaging system of claim 5, wherein:
   one of the first and second distal sections comprises a protrusion;
   the other one of the first and second distal sections comprises a recess configured to receive the protrusion; and
   the first distal section and the second distal section are configured to detachably couple to one another by interference fit between the protrusion and the recess.

8. The packaging system of claim 5, wherein the proximal section is pivotably coupled to the first distal section at the second boundary.

9. The packaging system of claim 8, further comprising a perforation at the second boundary being configured to facilitate detachment of the proximal section from the first distal section.

10. A surgical kit comprising:
    a tool including a working portion and a shaft; and
    a packaging system comprising:
       a casing comprising a distal section defining a cavity configured to receive the working portion of the tool; and
       a proximal section coupled to the distal section and being configured to receive the shaft of the tool, and the proximal section being configured to detach from the distal section; and
       wherein at least a portion of the distal section comprises a colored indicator to provide a visual indication of a location of the working portion of the tool.

11. A packaging system for a tool that has a working portion and a shaft, the packaging system comprising:
    a casing comprising a distal section defining a cavity configured to receive the working portion of the tool; and
    a proximal section coupled to the distal section and being configured to receive the shaft of the tool, and the proximal section being configured to detach from the distal section; and
    wherein instructions are provided on the proximal section and the instructions are configured to illustrate one or more steps for installing the tool to a surgical device.

12. The packaging system of claim 11, wherein the instructions provided on the proximal section are further defined as visual instructions.

13. The packaging system of claim 12, wherein the visual instructions illustrate steps for installing the tool to the surgical device.

14. The packaging system claim 13, wherein one of the illustrated steps is configured to instruct a proper manner to grasp the distal section for installing the tool to the surgical device.

15. The packaging system of claim 13, wherein one of the illustrated steps is configured to instruct a proper insertion of the shaft into the surgical device.

16. The packaging system of claim 11, wherein the distal section comprises:
    a first distal section comprising a first boundary and a second boundary;
    a second distal section coupled to the first distal section at the first boundary;
    the first and second distal sections being configured to collectively define the cavity that receives the working portion; and
    the first and second distal sections being configured to detachably couple to one another.

17. The packaging system claim 16, wherein the second distal section is pivotable relative to the first distal section at the first boundary such that the first distal section and the second distal section collectively provide a clamshell casing to the working portion of the tool.

18. The packaging system of claim 16, wherein:
    one of the first and second distal sections comprises a protrusion;
    the other one of the first and second distal sections comprises a recess configured to receive the protrusion; and
    the first distal section and the second distal section are configured to detachably couple to one another by interference fit between the protrusion and the recess.

19. The packaging system of claim 16, wherein the proximal section is pivotably coupled to the first distal section at the second boundary, and further comprising a perforation at the second boundary being configured to facilitate detachment of the proximal section from the first distal section.

20. A surgical kit comprising:
    a tool including a working portion and a shaft; and
    a packaging system comprising:
       a casing comprising a distal section defining a cavity configured to receive the working portion of the tool; and
       a proximal section coupled to the distal section and being configured to receive the shaft of the tool, and the proximal section being configured to detach from the distal section; and wherein instructions are provided on the proximal section and the instructions are configured to illustrate one or more steps for installing the tool to a surgical device.

* * * * *